US006294372B1

(12) United States Patent
Burian et al.

(10) Patent No.: US 6,294,372 B1
(45) Date of Patent: Sep. 25, 2001

(54) REPLICATION GENES AND GENE PRODUCTS FROM SMALL CRYPTIC PLASMIDS AND METHODS FOR CONSTRUCTING CONTROLLED-REPLICATION PLASMID VECTORS

(75) Inventors: Jàn Burian, Vancouver; William W. Kay, Victoria, both of (CA)

(73) Assignee: University of Victoria Innovation & Dev. Corp., British Columbia (CA)

( * ) Notice: Subject to any disclaimer, the term of this patent is extended or adjusted under 35 U.S.C. 154(b) by 0 days.

(21) Appl. No.: 09/042,071

(22) Filed: Mar. 13, 1998

Related U.S. Application Data

(60) Provisional application No. 60/040,722, filed on Mar. 14, 1997.

(51) Int. Cl.$^7$ .................................................. C12N 1/20
(52) U.S. Cl. ................................. 435/252.33; 435/320.1; 536/23.7
(58) Field of Search ............................. 435/320.1, 252.3, 435/252.33; 536/23.7, 24.1

(56) References Cited

U.S. PATENT DOCUMENTS 5,583,040 * 12/1996 Kaji ..................................... 435/252.3

OTHER PUBLICATIONS

Garcia de viedma et al. J. Molecular Biol. 247:211–223, 1995.*
Burian et al., Plasmid 37(1):2–14 (1997).*
Freifelder, *Molecular Biology:* A Comprehensive Introduction to Prokaryotes and Eukaryotes, Jones and Bartlett Publishers, Inc., Boston, 1983, pp. 797–799.*
George et al., "Current methods in sequence comparison and analysis," in Macromolecular Sequencing and Synthesis, Selected methods and Applications, 1988, D.H. Schlesinger (ed.), Alan R. Liss, Inc. New York NY, pp. 127–149.*
Boswell et al., "Sequence comparison and alignment: the measurement and interpretation of sequence similarity," in *Computational Molecular Biology:* Sources and Methods for Sequence Analysis, 1988, Arthur M. Lesk (ed.), Oxford University Press, New York, NY, pp. 161–178.*

* cited by examiner

*Primary Examiner*—Remy Yucel
(74) *Attorney, Agent, or Firm*—Seed IP Law Group

(57) ABSTRACT

The replication genes of small cryptic plasmids are isolated and used to construct controlled-replication plasmid vectors with the wide range of copy numbers controlled by defined helper plasmids. Controlled-replication vectors (RAMP vectors) can reach very high level of plasmid replication, which is not lethal to host unlike runaway replication vectors.

11 Claims, 13 Drawing Sheets

Fig. 7

Aminoacid sequence of RepA
MFIDSEKRLKQLSDEAKKNTEDLEEAKKNSRFTQVSPKGWERVRELLKDSQGISALKLYSFLAEHIDPTCGAVVA
DQQFLAEKLGVSRSTIIRWLNYLESKNALVRIPVAGKVCAYALDPHEVWKGYNTTKNHAAFVTKTLVNKDGDIQR
RIMAMFSN DNA sequence of pKL1
BASE COUNT      401 a     383 c     405 g     359 t
     1  CTACCGGAAA CCGTCTGGGG AGAACCCCAG ACCCCCATCG CTGCAACACC GACGGTCTAC
    61  GACCACCTAC CAACCGCATG GCTGCCTGTT CCGTGCAAAT GGGCTTTGCA GGGGGCTGGC
   121  GCGGTTCCTG GCGACCTGAA AGCCCCTGGT TAGGGGTATC GGCGCGCTTG ACCTCCTGAG
   181  AGCCTCTGTA AGCGTTTTTC GCGCCTTCCA TGCCCTGGCG GGCATCTAAA ACCCGTTTCG
   241  TGCGTCTGAG AGCTTTTGAG CGCGTTTGAG GGGCTATCTG GCGACTCATC CCCAAAAGAA
   301  CAACACCGGG ATCACCGACA ACATGCGAGA GGTGATCCCG CTCGCCGCAA GTCGATGACC
   361  GAGCGTAGCG AGCGAATCGA CGAGGAAGCG GAAGAGAACC GGAAGCCACA TTGAGCACTT
   421  ACGCACTGAT GCGGGGTGTC GGGGTGAAGC CCTGACCAAG TGGTAATCGT ATCGGCGTGC
   481  ATGCGCGGTT ATACGATTAC ACATCCTGTC CCGATTTCTG AGGCGTTTTA ACGGTGAACG
   541  GACGGCAAAA ACACGATGGA GCTGTTGAAC GTGAAAACCA CGAAATCTGG CAAAAATCAC
   601  GGCTGGCGAG GCTTGCATAG GAGTAAGCCA GTATACACTC CGCTATCGCT ACGTGACTGG
   661  TTCAGGGCTT CGCCCGACAC CCCCAAAGGG CGTTGCGTTG CACGCAACAC CCTTGCCTAG
   721  AATAGATCTT TTACGCCGAT TTGTAAGTGG TTGTTTTTTT AGTGTGTTTT TTATTTACCT
   781  GTCGCATCCA GGATGAAACA ACGTTGTCGC ATCCTGGATG CGACAACACG CAACAAGGTG
   841  TTGCACAGAT GTGTCATGAT GGCTTAGATT TGAACCAACG TTAGTGCATG GGATTTTCAG
   901  AGGGAAAAAA TCATGTTTAT TGATTCAGAA AAACGACTGA AACAACTTTC AGATGAGGCA
   961  AAGAAAAACA CCGAGGATCT CGAAGAAGCA AAGAAAAATT CAAGGTTTAC ACAGGTATCC
  1021  CCAAAAGGTT GGGAACGTGT TCGAGAGCTG CTGAAGGATA GCCAAGGCAT ATCAGCACTG
  1081  AAGCTGTACT CATTTTTAGC GGAGCATATC GATCCTACGT GTGGCGCTGT CGTTGCGGAT
  1141  CAGCAATTCC TAGCTGAAAA ACTTGGAGTT AGCAGAAGCA CAATTATTCG GTGGCTCAAT
  1201  TACTTAGAAT CAAAAAATGC ATTAGTTAGA ATCCCCGTTG CTGGTAAGGT TTGTGCGTAT
  1261  GCCCTCGATC CACATGAAGT CTGGAAGGGA TACAACACTA CGAAAAACCA TGCAGCGTTT
  1321  GTCACTAAAA CACTGGTCAA CAAAGACGGT GATATTCAGC GCCGAATCAT GGCCATGTTT
  1381  TCAAATTGAG CTAGCGGCAG GCGGACAATC AGGGGCTACG TGTTAACGTT CTGACCATGA
  1441  TTGTCTATCC TGCATTGCTC TTTTGCCGCC TCAAAATCCT TGCGTGTTT TTGCTCCCCG
  1501  TTCTCCAGAA AAAACCGAGC CGCCACGGTT CCGGCAGCGC CTTGAGCG

*Fig. 13*

Fragment of pC-28
429 bp (molecule 2781 bp)

Fragment of pC-hpro-28
642 bp (molecule 2994 bp)

Fragment of pC-rhpro-28
642 bp (molecule 2994 bp)

Fragment of pC-2hpro-28
855 bp (molecule 3207 bp)

Fragment of pC-2rhpro-28
855 bp (molecule 3207 bp)

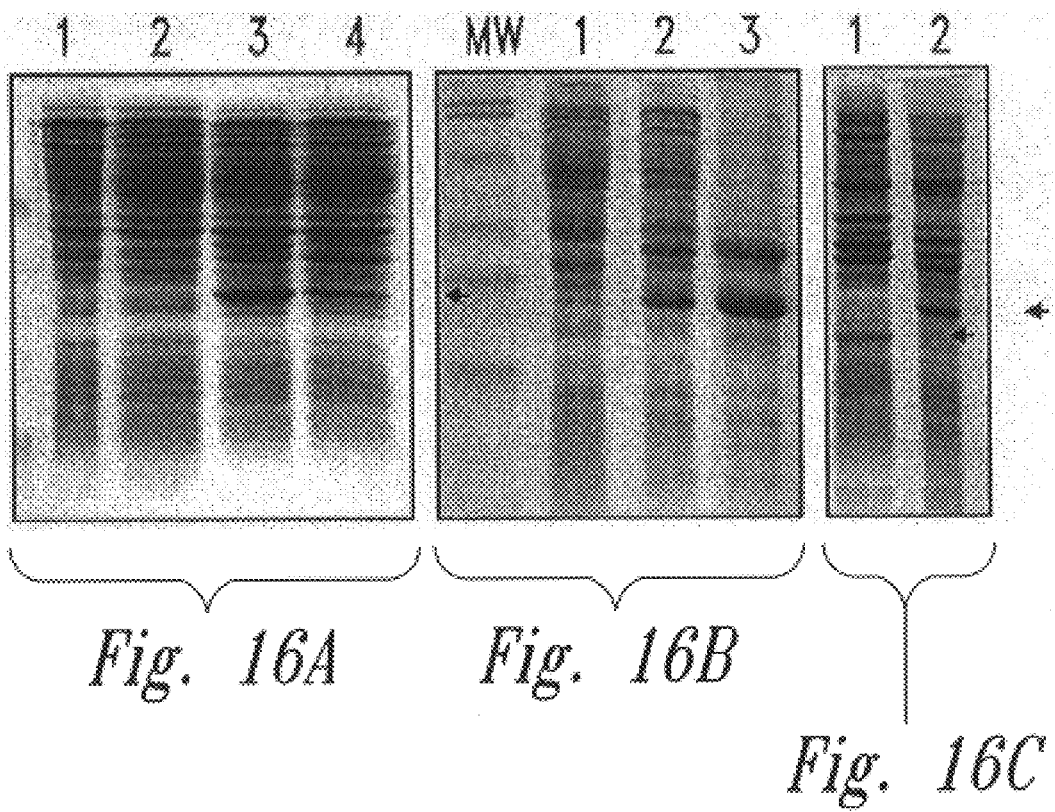
*Fig. 16A*  *Fig. 16B*  *Fig. 16C*
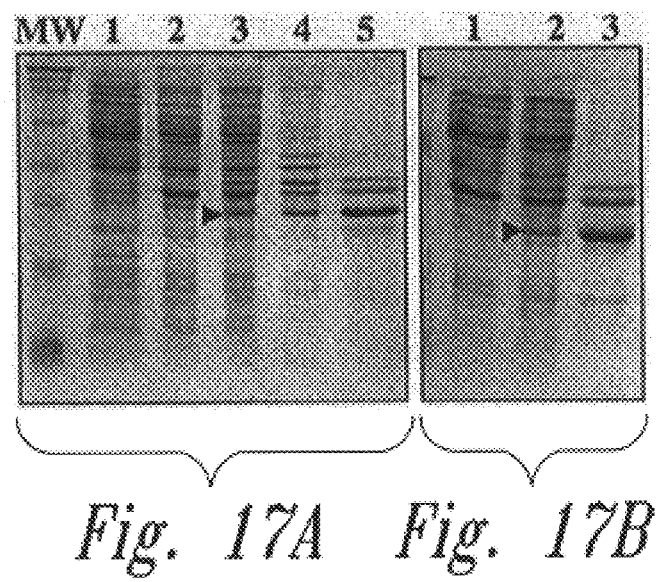
*Fig. 17A*  *Fig. 17B*

SEQUENCE LISTING (1) GENERAL INFORMATION:

(iii) NUMBER OF SEQUENCES: 52

(2) INFORMATION FOR SEQ ID NO: 1:

(i) SEQUENCE CHARACTERISTICS:
       (A) LENGTH: 99 base pairs
       (B) TYPE: nucleic acid
       (C) STRANDEDNESS: single
       (D) TOPOLOGY: linear (xi) SEQUENCE DESCRIPTION: SEQ ID NO: 1:

GATCACCGAC AACATGCGAG AGGTGATCCC GCTCGCCGCA AGTCGATGAC CGAGCGTAGC     60

GAGCGAATCG ACGAGGAAGC GGAAGAGAAC CGGAAGCCA                             99

(2) INFORMATION FOR SEQ ID NO: 2:

(i) SEQUENCE CHARACTERISTICS:
    (A) LENGTH: 94 base pairs
    (B) TYPE: nucleic acid
    (C) STRANDEDNESS: single
    (D) TOPOLOGY: linear (xi) SEQUENCE DESCRIPTION: SEQ ID NO: 2:

GGTCTGTCCT TTTACAGCCA GTAGTGCTCG CCGCAGTCGA GCGACAGGGC GAAGCCCTCG    60

AGTGAGCGAG GAAGCACCAG GGAACAGCAC TTAT    94

(2) INFORMATION FOR SEQ ID NO: 3:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 3:

GGTAGCGCTC GCCGCAGTCT CATGACCGAG CGTAGCGAGC GAATGAGCGA GGAAGCGCAA    60

AGGCGTCCGG TGGTG    75

(2) INFORMATION FOR SEQ ID NO: 4:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 4:

TCAGAAAAAA CGGTGCTCGC CGCAGACCGG TGACCGGGCG AAGCCCGCGA ACCGGCGAGG    60

AAGCGCAATG GATCTGTAAT CAC    83

(2) INFORMATION FOR SEQ ID NO: 5:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (xi) SEQUENCE DESCRIPTION: SEQ ID NO: 5:

AAATCTCCGC CCCGTTCGTA AGCCATTTCC GCTCGCCGCA GTCGAACGAC CGAGCGTAGC    60

GAGTCAGTGA GCGAGGAAGC GGAATATATC CTGTATCAC    99

(2) INFORMATION FOR SEQ ID NO: 6:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (xi) SEQUENCE DESCRIPTION: SEQ ID NO: 6:

TGTGTTACCG TTTTTGTGTG AGTCAGTACC GCTCGCCGCA GTCGAACGAC CGAGCGTAGC    60

GAGTCAGTGA GCGAGGAAGC GGAAAAGCGC TGGACGTGC    99

(2) INFORMATION FOR SEQ ID NO: 7:

(i) SEQUENCE CHARACTERISTICS:
        (A) LENGTH: 99 base pairs
        (B) TYPE: nucleic acid (C) STRANDEDNESS: single
        (D) TOPOLOGY: linear (xi) SEQUENCE DESCRIPTION: SEQ ID NO: 7:

AAATCTCCGC CCCGTTCGTA AGCCATTTCC GCTCGCCGCA GTCGAACGAC CGAGCGTAGC    60

GAGTCAGTGA GCGAGGAAGC GGAATATATC CTGTATCAC    99

(2) INFORMATION FOR SEQ ID NO: 8:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (xi) SEQUENCE DESCRIPTION: SEQ ID NO: 8:

AACTCTTCTG GTTTTGAGAA AGGAGACACC GCTCGCCGCA GCCGAACGAC CGAGTGTAGC    60

GAGTTAGTGA GCGAGGAAGC GGAACAGCAC AGGGATAAC    99

(2) INFORMATION FOR SEQ ID NO: 9:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 9:

CGTATTACCG CTTTTGAGTG AGCTGACACC GCTCGCCGCA AGTCGAACGA CCGAGCGTAG    60

CGAGTCAGTG AGCGAGGAAG CGGAAG    86

(2) INFORMATION FOR SEQ ID NO: 10:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (xi) SEQUENCE DESCRIPTION: SEQ ID NO: 10:

CGTATTACCG TCTTTGAGTG AGCTGATACC GCTCGCCGCA GCCGAACGAC CGAGCGTAGC    60

GAGTCAGTGA GCGAGGAAGC GGAAGAGCGC CGGAAGCTG    99

(2) INFORMATION FOR SEQ ID NO: 11:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (xi) SEQUENCE DESCRIPTION: SEQ ID NO: 11:

CCGCCTTTGA GTGAGCTGAT ACCGCTCGCC GCAGCCGAAC GACCGAGCGC AGCGAGTCAG    60

TGAGCGAGGA AGCGGAAGAG CGCCTGATGC GG    92

(2) INFORMATION FOR SEQ ID NO: 12:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 12:

GGAGTAAGCC AGTATACACT CCGCTATCGC TACGTGACTG GTTCAGGGCT TCGCCCGACA    60

(2) INFORMATION FOR SEQ ID NO: 13:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 13:

TAAGTAAGCC AGTATACACT CCGCTATCGC TACGTGACTG GGTCATGGCT GCGCCCCGAC    60

(2) INFORMATION FOR SEQ ID NO: 14:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 14:

ATAGTAAGCC AGTATACACT CCGCTAGCGC GACGTGACTG GTTCGGGCTG CGCCCCGAAA    60

(2) INFORMATION FOR SEQ ID NO: 15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 15:

TAGTTAAGCC AGTATACACT CCGCTATCGC TACGTGACTG GGTCATGGCT GCGCCCCGAC    60

(2) INFORMATION FOR SEQ ID NO: 16:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO: 16:

CGGGGTGTCG GGGTGAAGCC CTGACCAAGT GGTAATCGTA TCGGCGTGCA TGCGCGGTTA    60

TACGATTACA CATCCTGTCC CGATTTCTGA GGCGTTTT                            98

(2) INFORMATION FOR SEQ ID NO: 17:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 17:

CGGGGTGTCG GGGCGAAGCC CTGACCAGAT GGCAATTGTA ATAGCGTCGC GTGTGACGGT    60

ATTACAATTG CACATCCTGT CCCGTTTTTC GGGCCATTAT                         100

(2) INFORMATION FOR SEQ ID NO: 18:

(i) SEQUENCE CHARACTERISTICS:
        (A) LENGTH: 213 base pairs
        (B) TYPE: nucleic acid
        (C) STRANDEDNESS: single (D) TOPOLOGY: linear (xi) SEQUENCE DESCRIPTION: SEQ ID NO: 18:

| | | | | |
|---|---|---|---|---|
| AGATCTTTTA | CGCCGATTTG | TAAGTGGTTG | TTTTTTTAGT GTGTTTTTTA | TTTACCTGTC | 60 |
| GCATCCAGGA | TGAAAAAACG | TTGTCGCATC | CTGGATGCGA CAACACGCAA | CAAGGTGTTG | 120 |
| CACAGATGTG | TCATGATGGC | TTAGATTTGA | ACCAACGTTA GTGCATGGGA | TTTTCAGAGG | 180 |
| GAAAAAATCA | TGTTTATTGA | TTCAGAAAAA | CGA | | 213 |

(2) INFORMATION FOR SEQ ID NO: 19:

(i) SEQUENCE CHARACTERISTICS:
        (A) LENGTH: 1548 base pairs
        (B) TYPE: nucleic acid
        (C) STRANDEDNESS: single
        (D) TOPOLOGY: linear (xi) SEQUENCE DESCRIPTION: SEQ ID NO: 19:

| | | | | | |
|---|---|---|---|---|---|
| CTACCGGAAA | CCGTCTGGGG | AGAACCCCAG | ACCCCCATCG | CTGCAACACC GACGGTCTAC | 60 |
| GACCACCTAC | CAACCGCATG | GCTGCCTGTT | CCGTGCAAAT | GGGCTTTGCA GGGGGCTGGC | 120 |
| GCGGTTCCTG | GCGACCTGAA | AGCCCCTGGT | TAGGGGTATC | GGCGCGCTTG ACCTCCTGAG | 180 |
| AGCCTCTGTA | AGCGTTTTTC | GCGCCTTCCA | TGCCCTGGCG | GGCATCTAAA ACCCGTTTCG | 240 |
| TGCGTCTGAG | AGCTTTTGAG | CGCGTTTGAG | GGGCTATCTG | GCGACTCATC CCCAAAAGAA | 300 |
| CAACACCGGG | ATCACCGACA | ACATGCGAGA | GGTGATCCCG | CTCGCCGCAA GTCGATGACC | 360 |
| GAGCGTAGCG | AGCGAATCGA | CGAGGAAGCG | GAAGAGAACC | GGAAGCCACA TTGAGCACTT | 420 |
| ACGCACTGAT | GCGGGGTGTC | GGGGTGAAGC | CCTGACCAAG | TGGTAATCGT ATCGGCGTGC | 480 |
| ATGCGCGGTT | ATACGATTAC | ACATCCTGTC | CCGATTTCTG | AGGCGTTTTA ACGGTGAACG | 540 |
| GACGGCAAAA | ACACGATGGA | GCTGTTGAAC | GTGAAAACCA | CGAAATCTGG CAAAAATCAC | 600 |
| GGCTGGCGAG | GCTTGCATAG | GAGTAAGCCA | GTATACACTC | CGCTATCGCT ACGTGACTGG | 660 |
| TTCAGGGCTT | CGCCCGACAC | CCCCAAAGGG | CGTTGCGTTG | CACGCAACAC CCTTGCCTAG | 720 |
| AATAGATCTT | TTACGCCGAT | TTGTAAGTGG | TTGTTTTTTT | AGTGTGTTTT TTATTTACCT | 780 |
| GTCGCATCCA | GGATGAAACA | ACGTTGTCGC | ATCCTGGATG | CGACAACACG CAACAAGGTG | 840 |
| TTGCACAGAT | GTGTCATGAT | GGCTTAGATT | TGAACCAACG | TTAGTGCATG GGATTTTCAG | 900 |
| AGGGAAAAAA | TCATGTTTAT | TGATTCAGAA | AAACGACTGA | AACAACTTTC AGATGAGGCA | 960 |
| AGAAAAACA | CCGAGGATCT | CGAAGAAGCA | AGAAAAATT | CAAGGTTTAC ACAGGTATCC | 1020 |
| CCAAAAGGTT | GGGAACGTGT | TCGAGAGCTG | CTGAAGGATA | GCCAAGGCAT ATCAGCACTG | 1080 |
| AAGCTGTACT | CATTTTTAGC | GGAGCATATC | GATCCTACGT | GTGGCGCTGT CGTTGCGGAT | 1140 |
| CAGCAATTCC | TAGCTGAAAA | ACTTGGAGTT | AGCAGAAGCA | CAATTATTCG GTGGCTCAAT | 1200 |
| TACTTAGAAT | CAAAAAATGC | ATTAGTTAGA | ATCCCCGTTG | CTGGTAAGGT TTGTGCGTAT | 1260 |
| GCCCTCGATC | CACATGAAGT | CTGGAAGGGA | TACAACACTA | CGAAAAACCA TGCAGCGTTT | 1320 |
| GTCACTAAAA | CACTGGTCAA | CAAAGACGGT | GATATTCAGC | GCCGAATCAT GGCCATGTTT | 1380 |
| TCAAATTGAG | CTAGCGGCAG | GCGGACAATC | AGGGGCTACG | TGTTAACGTT CTGACCATGA | 1440 |
| TTGTCTATCC | TGCATTGCTC | TTTTGCCGCC | TCAAATCCT | TTGCGTGTTT TTGCTCCCCG | 1500 |
| TTCTCCAGAA | AAAACCGAGC | CGCCACGGTT | CCGGCAGCGC | CTTGAGCG | 1548 |

(2) INFORMATION FOR SEQ ID NO: 20:

(i) SEQUENCE CHARACTERISTICS:

(A) LENGTH: 158 amino acids
        (B) TYPE: amino acid
        (C) STRANDEDNESS:
        (D) TOPOLOGY: linear (xi) SEQUENCE DESCRIPTION: SEQ ID NO: 20:

Met Phe Ile Asp Ser Glu Lys Arg Leu Lys Gln Leu Ser Asp Glu Ala
1               5                   10                  15
Lys Lys Asn Thr Glu Asp Leu Glu Glu Ala Lys Lys Asn Ser Arg Phe
                20                  25                  30
Thr Gln Val Ser Pro Lys Gly Trp Glu Arg Val Arg Glu Leu Leu Lys
            35                  40                  45
Asp Ser Gln Gly Ile Ser Ala Leu Lys Leu Tyr Ser Phe Leu Ala Glu
50                      55                  60
His Ile Asp Pro Thr Cys Gly Ala Val Val Ala Asp Gln Gln Phe Leu
65                  70                  75                      80
Ala Glu Lys Leu Gly Val Ser Arg Ser Thr Ile Ile Arg Trp Leu Asn
                85                  90                  95
Tyr Leu Glu Ser Lys Asn Ala Leu Val Arg Ile Pro Val Ala Gly Lys
            100                 105                 110
Val Cys Ala Tyr Ala Leu Asp Pro His Glu Val Trp Lys Gly Tyr Asn
            115                 120                 125
Thr Thr Lys Asn His Ala Ala Phe Val Thr Lys Thr Leu Val Asn Lys
        130                 135                 140
Asp Gly Asp Ile Gln Arg Arg Ile Met Ala Met Phe Ser Asn
145                 150                 155

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 21:

GGGGAACCCC AGAATTCTGC GGGCTCCC                                              28

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 22:

GATTGGATCC AACGTTAGTG C                                                     21

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 23:

GCCAAGATCT AATACGACTC AC                                                    22

(2) INFORMATION FOR SEQ ID NO: 24:

(i) SEQUENCE CHARACTERISTICS:
 (A) LENGTH: 26 base pairs
 (B) TYPE: nucleic acid
 (C) STRANDEDNESS: single
 (D) TOPOLOGY: linear (xi) SEQUENCE DESCRIPTION: SEQ ID NO: 24:

CCCTCTGAGG ATCCCATGCA CTAACG                26

(2) INFORMATION FOR SEQ ID NO: 25:

(i) SEQUENCE CHARACTERISTICS:
 (A) LENGTH: 13 base pairs
 (B) TYPE: nucleic acid
 (C) STRANDEDNESS: single
 (D) TOPOLOGY: linear (xi) SEQUENCE DESCRIPTION: SEQ ID NO: 25:

TAAGTGGTTG TTT                13

(2) INFORMATION FOR SEQ ID NO: 26:

(i) SEQUENCE CHARACTERISTICS:
 (A) LENGTH: 48 amino acids
 (B) TYPE: amino acid
 (C) STRANDEDNESS:
 (D) TOPOLOGY: linear (xi) SEQUENCE DESCRIPTION: SEQ ID NO: 26:

Met Phe Ile Asp Ser Glu Lys Arg Leu Lys Gln Leu Ser Asp Glu Ala
1               5                  10                  15

Lys Lys Asn Thr Glu Asp Leu Glu Glu Ala Lys Lys Asn Ser Arg Phe
        20                  25                  30

Thr Gln Val Ser Lys Pro Gly Trp Glu Arg Val Arg Glu Leu Leu Lys
        35                  40                  45

(2) INFORMATION FOR SEQ ID NO: 27:

(i) SEQUENCE CHARACTERISTICS:
 (A) LENGTH: 11 base pairs
 (B) TYPE: nucleic acid
 (C) STRANDEDNESS: single
 (D) TOPOLOGY: linear (xi) SEQUENCE DESCRIPTION: SEQ ID NO: 27:

CATCCAGGAT G                11

(2) INFORMATION FOR SEQ ID NO: 28:

(i) SEQUENCE CHARACTERISTICS:
 (A) LENGTH: 10 base pairs
 (B) TYPE: nucleic acid
 (C) STRANDEDNESS: single
 (D) TOPOLOGY: linear (xi) SEQUENCE DESCRIPTION: SEQ ID NO: 28:

ACAACGTTGT                10

(2) INFORMATION FOR SEQ ID NO: 29:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (xi) SEQUENCE DESCRIPTION: SEQ ID NO: 29:

```
TCGAGCTCGG TACCCGG                                                      17
```

(2) INFORMATION FOR SEQ ID NO: 30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 30:

```
TGGCTTAGAA TTCAACCAAC GTTAG                                             25
```

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 31:

```
AGAACTCGAG CAGCTGAAGC TTAG                                              24
```

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 32:

```
CGTTGCAGAT CTACATCACC ATCACCATCA                                        30
```

(2) INFORMATION FOR SEQ ID NO: 33:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 33:

```
TGCGGATCCC CGTTTTTCCT TGAGCCTGGA TGCTTTGGAG CCAACGTTTC                  50
```

(2) INFORMATION FOR SEQ ID NO: 34:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO: 34:

```
Lys Trp Lys Leu Phe Lys Lys Ile Gly Ile Gly Ala Val Leu Lys Val
1               5                   10                  15

Leu Thr Thr Gly Leu Pro Ala Leu Lys Leu Thr Asn
            20                  25
```

(2) INFORMATION FOR SEQ ID NO: 35:

(i) SEQUENCE CHARACTERISTICS:
        (A) LENGTH: 18 amino acids
        (B) TYPE: amino acid
        (C) STRANDEDNESS:

(D) TOPOLOGY: linear (xi) SEQUENCE DESCRIPTION: SEQ ID NO: 35:

Gly Lys Pro Arg Pro Tyr Ser Pro Ile Pro Thr Ser Pro Arg Pro Ile
1               5                   10                  15

Arg Tyr (2) INFORMATION FOR SEQ ID NO: 36:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 36:

Ile Leu Lys Lys Trp Pro Trp Trp Pro Trp Arg Arg Lys
1               5                   10

(2) INFORMATION FOR SEQ ID NO: 37:

(i) SEQUENCE CHARACTERISTICS:
        (A) LENGTH: 53 amino acids
        (B) TYPE: amino acid
        (C) STRANDEDNESS:
        (D) TOPOLOGY: linear (xi) SEQUENCE DESCRIPTION: SEQ ID NO: 37:

Met Phe Ile Asp Ser Glu Lys Arg Leu Lys Gln Leu Ser Asp Glu Ala
1               5                   10                  15

Lys Lys Asn Thr Glu Asp Pro His Met Lys Trp Lys Leu Phe Lys Lys
                20                  25                  30

Ile Gly Ile Gly Ala Val Leu Lys Val Leu Thr Thr Gly Leu Pro Ala
                35                  40                  45

Leu Lys Leu Thr Asn
                50

(2) INFORMATION FOR SEQ ID NO: 38:

(i) SEQUENCE CHARACTERISTICS:
        (A) LENGTH: 72 amino acids
        (B) TYPE: amino acid
        (C) STRANDEDNESS:
        (D) TOPOLOGY: linear (xi) SEQUENCE DESCRIPTION: SEQ ID NO: 38:

His His His His His His Arg Thr Leu Ala Ile Leu Ala Ala Ile Leu
1               5                   10                  15

Leu Val Ala Leu Gln Ala Gln Ala Glu Pro Leu Gln Ala Arg Ala Asp
                20                  25                  30

Glu Val Ala Ala Ala Pro Glu Gln Ile Ala Ala Asp Ile Pro Glu Val
                35                  40                  45

Val Val Ser Leu Ala Trp Asp Glu Thr Leu Ala Pro Lys His Pro Gly
                50                  55                  60

Ser Arg Lys Asn Gly Asp Pro His
65                  70

(2) INFORMATION FOR SEQ ID NO: 39:

(i) SEQUENCE CHARACTERISTICS:
        (A) LENGTH: 124 amino acids
        (B) TYPE: amino acid
        (C) STRANDEDNESS:

(D) TOPOLOGY: linear (xi) SEQUENCE DESCRIPTION: SEQ ID NO: 39:

Met Phe Ile Asp Ser Glu Lys Arg Leu Lys Gln Leu Ser Asp Glu Ala
1               5                   10                  15

Lys Lys Asn Thr Glu Asp Pro His His His His His His Arg Thr Leu
                20                  25                  30

Ala Ile Leu Ala Ala Ile Leu Leu Val Ala Leu Gln Ala Gln Ala Glu
            35                  40                  45

Pro Leu Gln Ala Arg Ala Asp Glu Val Ala Ala Pro Glu Gln Ile
    50                  55                  60

Ala Ala Asp Ile Pro Glu Val Val Val Ser Leu Ala Trp Asp Glu Thr
65                  70                  75                  80

Leu Ala Pro Lys His Pro Gly Ser Arg Lys Asn Gly Asp Pro His Met
                85                  90                  95

Lys Trp Lys Leu Phe Lys Lys Ile Gly Ile Gly Ala Val Leu Lys Val
                100                 105                 110

Leu Thr Thr Gly Leu Pro Ala Leu Lys Leu Thr Asn
            115                 120

(2) INFORMATION FOR SEQ ID NO: 40:

(i) SEQUENCE CHARACTERISTICS:
        (A) LENGTH: 195 amino acids
        (B) TYPE: amino acid
        (C) STRANDEDNESS:
        (D) TOPOLOGY: linear (xi) SEQUENCE DESCRIPTION: SEQ ID NO: 40:

Met Phe Ile Asp Ser Glu Lys Arg Leu Lys Gln Leu Ser Asp Glu Ala
1               5                   10                  15

Lys Lys Asn Thr Glu Asp Pro His His His His His His Arg Thr Leu
                20                  25                  30

Ala Ile Leu Ala Ala Ile Leu Leu Val Ala Leu Gln Ala Gln Ala Glu
            35                  40                  45

Pro Leu Gln Ala Arg Ala Asp Glu Val Ala Ala Pro Glu Gln Ile
    50                  55                  60

Ala Ala Asp Ile Pro Glu Val Val Val Ser Leu Ala Trp Asp Glu Thr
65                  70                  75                  80

Leu Ala Pro Lys His Pro Gly Ser Arg Lys Asn Gly Asp Pro His His
                85                  90                  95

His His His His Arg Thr Leu Ala Ile Leu Ala Ala Ile Leu Leu Val
                100                 105                 110

Ala Leu Gln Ala Gln Ala Glu Pro Leu Gln Ala Arg Ala Asp Glu Val
            115                 120                 125

Ala Ala Ala Pro Glu Gln Ile Ala Ala Asp Ile Pro Glu Val Val Val
        130                 135                 140

Ser Leu Ala Trp Asp Glu Thr Leu Ala Pro Lys His Pro Gly Ser Arg
145                 150                 155                 160

Lys Asn Gly Asp Pro His Met Lys Trp Lys Leu Phe Lys Lys Ile Gly
                165                 170                 175

Ile Gly Ala Val Leu Lys Val Leu Thr Thr Gly Leu Pro Ala Leu Lys
            180                 185                 190

Leu Thr Asn
    195

(2) INFORMATION FOR SEQ ID NO: 41:

(i) SEQUENCE CHARACTERISTICS:
        (A) LENGTH: 195 amino acids
        (B) TYPE: amino acid
        (C) STRANDEDNESS:
        (D) TOPOLOGY: linear (xi) SEQUENCE DESCRIPTION: SEQ ID NO: 41:

```
Met Phe Ile Asp Ser Glu Lys Arg Leu Lys Gln Leu Ser Asp Glu Ala
1               5                   10                  15

Lys Lys Asn Thr Glu Asp Pro Arg Phe Ser Leu Ser Leu Asp Ala Leu
            20                  25                  30

Glu Pro Thr Phe Arg Pro Met Gln Gly Lys Gln Pro Leu Leu Gly Cys
        35                  40                  45

Gln Leu Gln Ser Ala Pro Gly Leu Leu Gln Pro His Gln Leu Leu Pro
    50                  55                  60

Gly Val Ala Gln Pro Gly Pro Ala Gly Pro Pro Gly Glu Trp Gln Gln
65                  70                  75                  80

Gly Trp Arg Gly Ser Cys Asp Gly Asp Gly Asp Val Asp Pro Arg Phe
                85                  90                  95

Ser Leu Ser Leu Asp Ala Leu Glu Pro Thr Phe Arg Pro Met Gln Gly
            100                 105                 110

Lys Gln Pro Leu Leu Gly Cys Gln Leu Gln Ser Ala Pro Gly Leu Leu
        115                 120                 125

Gln Pro His Gln Leu Leu Pro Gly Val Ala Gln Pro Gly Pro Ala Gly
    130                 135                 140

Pro Pro Gly Glu Trp Gln Gln Gly Trp Arg Gly Ser Cys Asp Gly Asp
145                 150                 155                 160

Gly Asp Val Asp Pro His Met Lys Trp Lys Leu Phe Lys Lys Ile Gly
                165                 170                 175

Ile Gly Ala Val Leu Lys Val Leu Thr Thr Gly Leu Pro Ala Leu Lys
            180                 185                 190

Leu Thr Asn
        195
```

(2) INFORMATION FOR SEQ ID NO: 42:

(i) SEQUENCE CHARACTERISTICS:
        (A) LENGTH: 178 amino acids
        (B) TYPE: amino acid
        (C) STRANDEDNESS:
        (D) TOPOLOGY: linear (xi) SEQUENCE DESCRIPTION: SEQ ID NO: 42:

```
Met Phe Ile Asp Ser Glu Lys Arg Leu Lys Gln Leu Ser Asp Glu Ala
1               5                   10                  15

Lys Lys Asn Thr Glu Asp Leu Glu Glu Ala Lys Lys Asn Ser Arg Phe
            20                  25                  30

Thr Gln Val Ser Pro Lys Gly Trp Glu Arg Val Arg Glu Leu Leu Lys
        35                  40                  45

Asp Ser Gln Gly Ile Ser Ala Leu Lys Leu Tyr Ser Phe Leu Ala Asp
    50                  55                  60

His Ile Asp Pro Thr Cys Gly Ala Val Val Ala Asp Pro His His His
65                  70                  75                  80

His His His Arg Thr Leu Ala Ile Leu Ala Ala Ile Leu Leu Val Ala
                85                  90                  95

Leu Gln Ala Gln Ala Glu Pro Leu Gln Ala Arg Ala Asp Glu Val Ala
```

```
                100             105             110
Ala Ala Pro Glu Gln Ile Ala Ala Asp Ile Pro Glu Val Val Ser
        115             120             125

Leu Ala Trp Asp Glu Thr Leu Ala Pro Lys His Pro Gly Ser Arg Lys
        130             135             140

Asn Gly Asp Pro His Met Lys Trp Lys Leu Phe Lys Lys Ile Gly Ile
145             150             155             160

Gly Ala Val Leu Lys Val Leu Thr Thr Gly Leu Pro Ala Leu Lys Leu
                165             170             175

Thr Asn
```

(2) INFORMATION FOR SEQ ID NO: 43:

(i) SEQUENCE CHARACTERISTICS:
        (A) LENGTH: 178 amino acids
        (B) TYPE: amino acid
        (C) STRANDEDNESS:
        (D) TOPOLOGY: linear (xi) SEQUENCE DESCRIPTION: SEQ ID NO: 43:

```
Met Phe Ile Asp Ser Glu Lys Arg Leu Lys Gln Leu Ser Asp Glu Ala
1               5               10              15

Lys Lys Asn Thr Glu Asp Leu Glu Glu Ala Lys Lys Asn Ser Arg Phe
            20              25              30

Thr Gln Val Ser Pro Lys Gly Trp Glu Arg Val Arg Glu Leu Leu Lys
        35              40              45

Asp Ser Gln Gly Ile Ser Ala Leu Lys Leu Tyr Ser Phe Leu Ala Asp
    50              55              60

His Ile Asp Pro Thr Cys Gly Ala Val Val Ala Asp Pro Arg Phe Ser
65              70              75              80

Leu Ser Leu Asp Ala Leu Glu Pro Thr Phe Arg Pro Met Gln Gly Lys
            85              90              95

Gln Pro Leu Leu Gly Cys Gln Leu Gln Ser Ala Pro Gly Leu Leu Gln
        100             105             110

Pro His Gln Leu Leu Pro Gly Val Ala Gln Pro Gly Pro Ala Gly Pro
    115             120             125

Pro Gly Glu Trp Gln Gln Gly Trp Arg Gly Ser Cys Asp Gly Asp Gly
        130             135             140

Asp Val Asp Pro His Met Lys Trp Lys Leu Phe Lys Lys Ile Gly Ile
145             150             155             160

Gly Ala Val Leu Lys Val Leu Thr Thr Gly Leu Pro Ala Leu Lys Leu
                165             170             175

Thr Asn
```

(2) INFORMATION FOR SEQ ID NO: 44:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO: 44:

```
ACCATCACAG GACCCTCGCC ATCCTTGCTG CCATTCTCCT GGTGGCCCTG CAGGCCCAGG     60

CTGAGCCACT CCAGGCAAGA GCTGATGAGG TTGCAGCAGC CCCGG                    105
```

(2) INFORMATION FOR SEQ ID NO: 45:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (xi) SEQUENCE DESCRIPTION: SEQ ID NO: 45:

TGAGCCTGGA TGCTTTGGAG CCAACGTTTC GTCCCATGCA AGGGAAACAA CCACTTCTGG    60

GATGTCAGCT GCAATCTGCT CCGGGGCTGC TGCAACCTCA TC    102

(2) INFORMATION FOR SEQ ID NO: 46:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 46:

CGAGGATCCA CATCACCATC ACCATCACAG GACCCTCGCC ATCCTTGCTG    50

(2) INFORMATION FOR SEQ ID NO: 47:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 47:

TGCGGATCCC CGTTTTTCCT TGAGCCTGGA TGCTTTGGAG CCAACGTTTC    50

(2) INFORMATION FOR SEQ ID NO: 48:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 48:

TTTAACGGGG ATCCGCATAT GGGTAAACCG CGTCCGTATA GCCCGATCCC GACCAGCCCG    60

CGTCCGATCC GTTATTAAGC TTGATATCTT GGTACCTGCG    100

(2) INFORMATION FOR SEQ ID NO: 49:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 49:

TTTAACGGGG ATCCGTCTCA TATGATCCTG AAAAAATGGC CGTGGTGGCC GTGGCGTCGT    60

AAATAAGCTT GATATCTTGG TACCTGCG    88

(2) INFORMATION FOR SEQ ID NO: 50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 50:

-continued

```
TTTAACGGGG ATCCGCATAT G                                        21

(2) INFORMATION FOR SEQ ID NO: 51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 51:

CGCAGGTACC AAGATATCAA GCTTA                                    25

(2) INFORMATION FOR SEQ ID NO: 52:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO: 52:

Met Phe Ile Asp Ser Glu Lys Arg
1               5
```

1

REPLICATION GENES AND GENE PRODUCTS FROM SMALL CRYPTIC PLASMIDS AND METHODS FOR CONSTRUCTING CONTROLLED-REPLICATION PLASMID VECTORS

CROSS-REFERENCE TO RELATED APPLICATION

This application claims the benefit of U.S. Provisional Application Ser. No. 60/040,722, filed Mar. 14, 1997, which application is hereby incorporated by reference in its entirety.

TECHNICAL FIELD

This invention relates generally to replication genes and gene products identified in small cryptic plasmids, and more specifically, to methods for constructing controlled-replication plasmid vectors which are not lethal to the host and capable of very high levels of replication.

BACKGROUND OF THE INVENTION

The production of large quantities of proteins for use as therapeutics, additives, and other myriad applications remains a challenge. Large-scale fermentation is a commonly used method, but is expensive and difficult to maintain the required quality and consistency of product. When producing proteins in bacteria, vectors that have a high copy number are generally sought because the amount of protein is often directly proportional to gene dosage.

DNA vaccination, perhaps more precisely called DNA-mediated immunization, refers to the direct introduction into a living species of plasmid or even non-plasmid DNA (or RNA) which is able to cause expression of antigenic protein (s) or peptide(s) in the newly transfected cells. Presentation of DNA into tissues of the host species may be by needle injection, particle bombardment or even orally using various DNA formulations which may be either "naked" DNA, coated microparticles, or via liposomes or biodegradable microcapsules or microspheres. In any case relatively large quantities of purified plasmid DNA are required for production of these vaccines.

Runaway replication plasmid vectors have been developed for expression of genes in bacteria. These vectors are based on plasmids, such as RI in which an antisense RNA transcript is a negative regulator of repA translation and a product of the copB gene, is a repressor of transcription of repA. RepA protein, which functions in cis, is necessary and rate-limiting for replication. The copy number of the plasmid is determined by the relative levels of the antisense RNA and RepA mRNA. If the antisense RNA levels decrease and RepA mRNA increases, expansive plasmid replication results. This is achieved by defined temperature sensitive mutations in the plasmid regulatory region or by insertion of an additional inducible promoter (ex. λ promoter) upstream of repA gene. Plasmid replication is then temperature sensitive and is induced to high levels at 42° C. Moreover, protein synthesis is concomitant with replication, leading to high levels of proteins that are encoded by the vector.

While these runaway-replication plasmid vectors have been used to produce a variety of proteins, including hGCSF and somatotropin, the amount of protein produced has been limited by such factors as the copy number (about 1000 copies per cell), and cell death resulting from runaway replication, thus preventing the use of continuous fermentation techniques. Thus, there is a need for expression vector systems without these limitations.

The present invention discloses genes and gene products from small cryptic plasmids and their use in constructing easily controlled, stable, high copy number replication vectors, and further provides other related advantages.

SUMMARY OF THE INVENTION

Within one aspect of the present invention, controlled-replication plasmid vectors are provided comprising a replication origin region of small cryptic plasmids and a gene encoding the RepA protein. In preferred embodiments the gene encoding RepA is under control of an inducible promoter.

These and other aspects of the present invention will become evident upon reference to the following detailed description and attached drawings. In addition, various references are set forth below which describe in more detail certain procedures or compositions, and are therefore incorporated by reference in their entirety.

Figure 1:
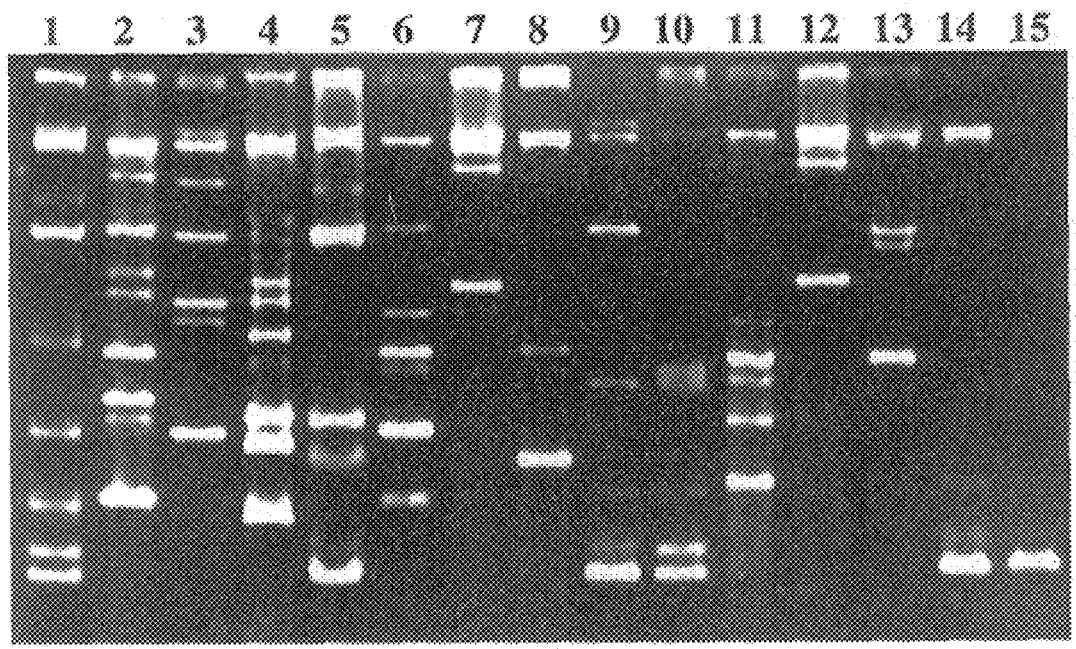
FIG. 1. Plasmid profiles of clinical strains of E. coli. Clinical strains of E. coli isolated from urinal tracts of human patients (lane 1–15). Fifteen strains represent a random sample from eighty-one analyzed clinical strains. Plasmid DNA isolated from E. coli KL4 is in lane 1.

pKL1 is a the wild type, small cryptic plasmid pC is based on vector pTZ19R and contains the Sau3AI fragment C of pKL1 pC72 is based on vector pSP72 and contains the Sau3AI fragment C of pKL1 recloned from pC pC72lacTL is based on vector pSP72 and contains the Sau3AI fragment C of pKL1 recloned from pC; lacZ was fused to repA after the 21st triplet.

pAClac184 is based on pACYC1854 and contains the Sau3AI fragment C of pKL1 recloned with lacZ fused to repA after 21st triplet recloned from pC72lacTL pB1 & pB2 are based on pTZ19R and contain the Sau3A fragment B of pKL1 in two different orientations pTZKL1 contains the EcoRI fragment KL1 of plasmid pKL1::Tn1737Km cloned into the EcoRI cloning site of pTZ19R. This fragment represents the whole pKL1 sequence. pTZKL1 contains two origins of replication, one from pTZ19R and one from pKL1. These plasmids can replicate inpolA1 hosts. Orientation of the KL1 insert does not allow expression of the repA gene from the T7 promoter of pTZ19R.

pBGL-R is based on pTZ19R and contains the BglII-BamHI fragment of pTZKL1 with the repA gene of pKL1, which can be expressed via induction of the T7 promoter of pTZ19R or lacP. It is a helper plasmid for amplification of pKL1 copy number.

pBGL-F is based on pTZ19R and contains the same fragment as pBGL-R, but in opposite orientation; repA cannot be expressed from T7 or lacP promoters. This plasmid binds RepA and can eliminate pKL1.

pBGL73 is based on pSP73 and contains the same insert as pBGL-R with the repA gene of pKL1, which can be expressed via induction of the T7 promoter of pTZ19R. In the absence of T7 induction this plasmid binds RepA and can eliminate pKL1. When the T7 system is induced, it is a helper plasmid for amplification of pKL1 copy number. pACBGL184 is based on the low copy number plasmid pACYC184 and contains the same insert as pBGL-R, but no external promoter. This plasmid binds RepA and can suppress the copy number of pKL1.

pREP1 is based on pTZ19R and contains a repA fragment of pKL1 created by PCR. repA can be expressed via induction of the T7 promoter of pTZ19R or lacP. It is a helper plasmid for amplification of pKL1 copy number.

pUKREP21 is based on pUK21 and contains the same fragment as pREP1. repA can be expressed via induction of lacP' (mutant promoter with 15% wild type activity). It is a helper plasmid for amplification of pKL1 copy number.

pPDREP1 is based on pPD1 and contains the same fragment as pREP1. repA can be expressed via induction of lacP. It is a helper plasmid for amplification of pKL1 copy number.

pKREP194 is based on pK194 and contains the same fragment as pREP1. repA can be expressed via induction of lacP. It is a helper plasmid for amplification of pKL1 copy number.

FIGS. 7A, B, and C. DNA sequence of selected regions of pKL1 (SEQ ID Nos: 1, 12 and 16). Regions of homology with ssi (A), ori ColA, ColD and ColE1 (pBR322) (B) and oriT (C) are shown. (A) dnaBCG is the consensus sequence of dnaB, dnaC and dnaG protein-dependent initiation signal; n' PRS is putative n' protein (PriA) recognition site; ECSSIA—E. coli F plasmid ssiA. (134 bp, EMBL ACC D90179); (;SEQ ID NO:2)ECSSIA03—E. coli plasmid ColE2 ssiA. (76 bp, EMBL ACC D90186); (;SEQ ID NO:3) ECSSIF—E. coli F plasmid ssiF. (100 bp,.EMBL ACCD90181) (;SEQ ID NO:4) ECP15A—E. coli plasmid p15A fragment specifying the origin of replication. (1025 bp, EMBL ACC V00309, J01748); (; SEQ ID NO:5) PCECORI—plasmid ColE1 origin of replication. (275 bp, EMBL ACC M25196); (SEQ ID NO:6) PPODR—plasmid p15A primer precursor DNA 3' to the origin of replication. (201 bp, EMBL ACC M24166) (SEQ ID NO:7); PROR—plasmid R485 replication origin region. (591 bp, EMBL ACC MI 1688) (SEQ ID NO:8); AROR—plasmid RSF1030 replication origin region with RNA I and primer precursor transcript (853 bp, EMBL ACC J101784) (SEQ ID NO:9); SFRAMC—*Salmonella flexneri* 2 MDa plasmid DNA associated with reactive arthritis. (3048 bp, EMBL ACC M25995) (SEQ ID NO:10); PRREP—plasmid R100 replication-associated protein (repA) genes, complete. (7053 bp, EMBL ACC M26840) (SEQ ID NO:11); pBR322—(4361 bp, gb SYNPBR322). (B) PCORIA02—plasmid ColD replication origin region, (1099 bp, EMBL ACC M12575) (SEQ ID NO:13); PCORIA03—plasmid ColA replication origin region, (1033 bp, EMBL ACC M12574); pBR322—(4361 bp, gb SYNPBR322) (;SEQ ID NO:15). (C) Inverted repeats located on oriT and pKL1 are indicated by arrows. The perfect inverted repeats of pKL1 are indicated by bold. oriT—plasmid R64 from *Salmonella typhimurium*) oriT region DNA, (842 bp) (SEQ ID NO:17)

Figure 8:
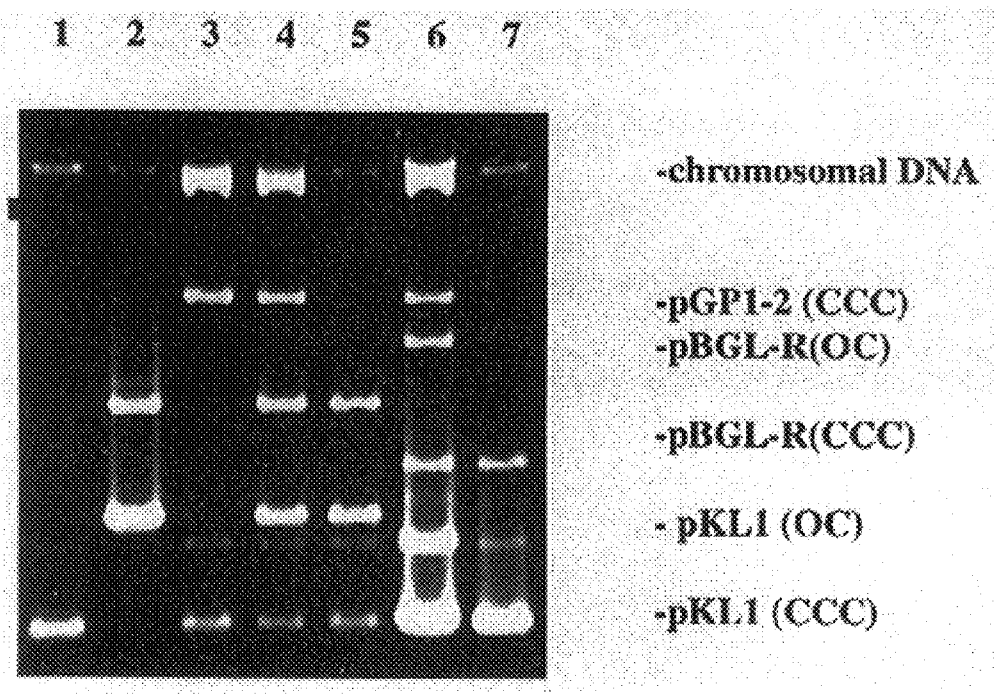

FIG. 8. Effect of RepA on pKL1 replication. Plasmid DNAs were separated by agarose electrophoresis and stained with ethidium bromide. The location of each plasmid DNA is indicated. Lane 1—pKL1, cultivated at 37° C.; Lane 2—pTZ19R, cultivated at 37° C.; Lane 3—pGP1-2 and pKL1, cultivated at 30° C.; Lane 4—pGP1-2, pTZ19R and pKL1, cultivated at 30° C.; Lane 5—pTZ19R and pKL1, cultivated at 37° C. ; Lane 6—pGP1-2, pBGL-R and pKL1, cultivated at 30° C.; Lane 7—pBGL-R and pKL1, cultivated at 37° C. CCC is covalently closed circular form of plasmid DNA, OC is open form of plasmid DNA.

Figure 9:
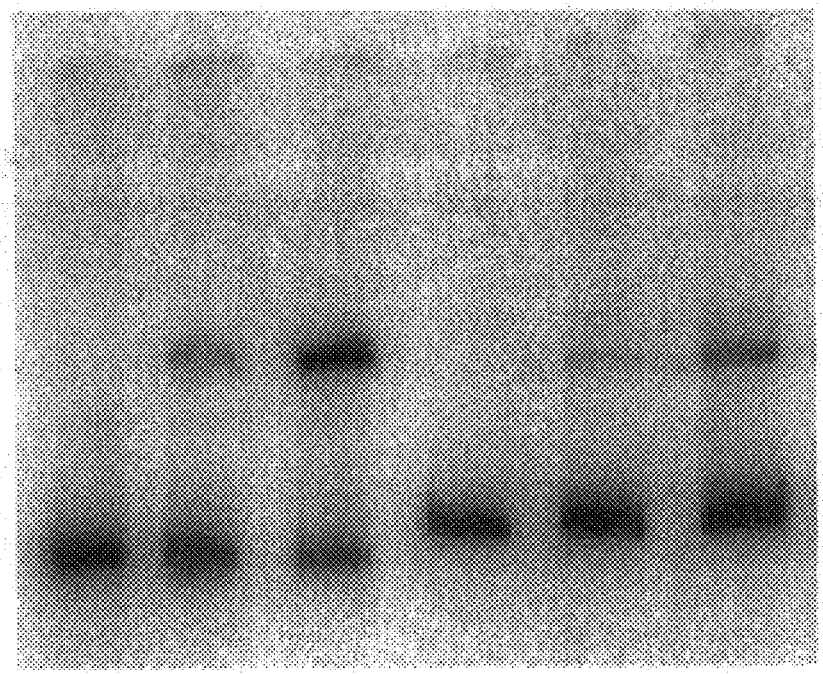

FIG. 9. Gel retardation assay with integration host factor (IHF). [$\alpha$-$^{32}$P]-dATP labeled DNA fragments were incubated with IHF, separated by electrophoresis and examined by autoradiography. Lane 1—HindIII fragment from pGP1261 with IHF binding site; Lane 2—HindIII fragment from pGP1261 and 50 pmol of IHF; Lane 3—HindIII fragment from pGP1261 and 100 pmol of IHF; Lane 4—Sau3AI fragment C from pKL1; Lane 5—Sau3AI fragment C from pKL1 and 50 pmol of IHF; Lane 6—Sau3AI fragment C from pKL1 and 100 pmol of IHF.

Figure 10:
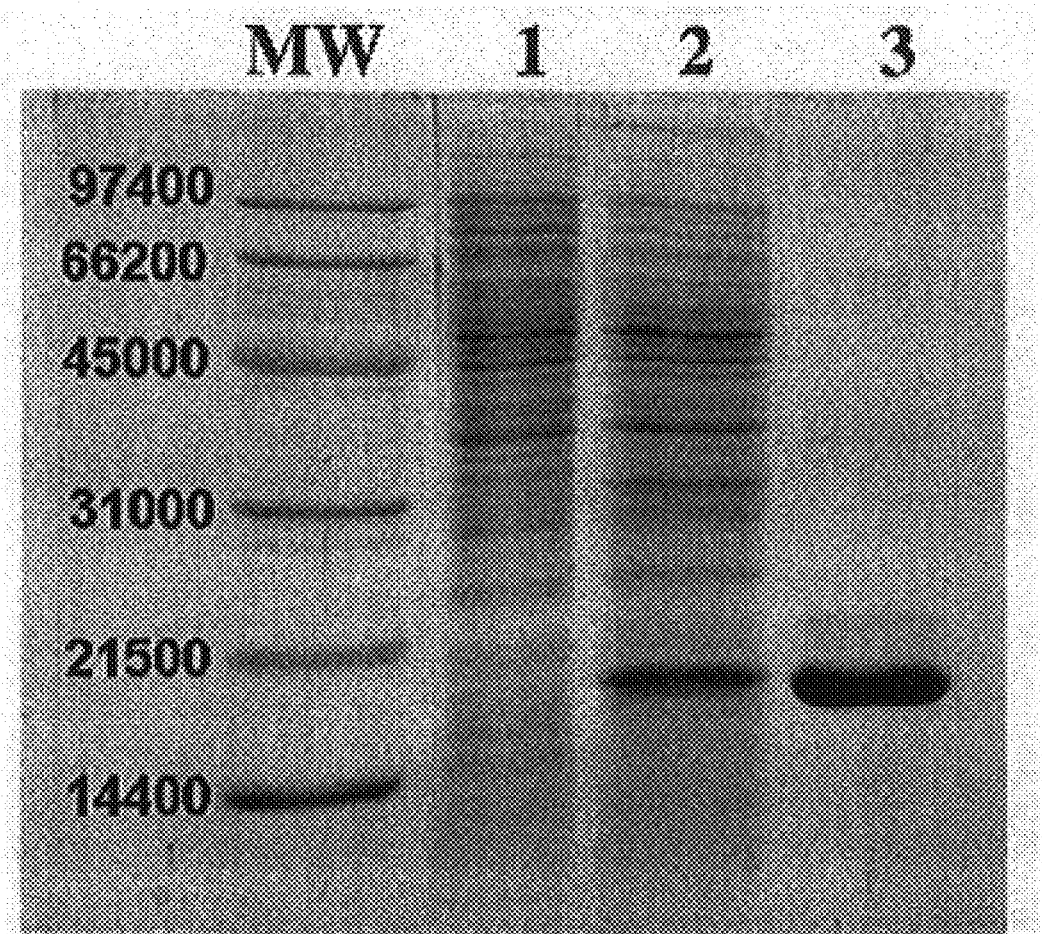

FIG. 10. Expression and purification of RepA. Whole cell lysates representing a expression strain before and after temperature induction were analyzed by SDS-PAGE.

Molecular weight standards are as noted. Standard proteins (MW); *E. coli* XL1 Blue cells cultivated at 37° C. (lane 1); *E. coli* XL1 Blue cells containing pGP1-2 and pBGL-R cultivated at 30° C. and shifted to 42° C. for 2 h (lane 2). Purified RepA (lane 3).

Figure 11:
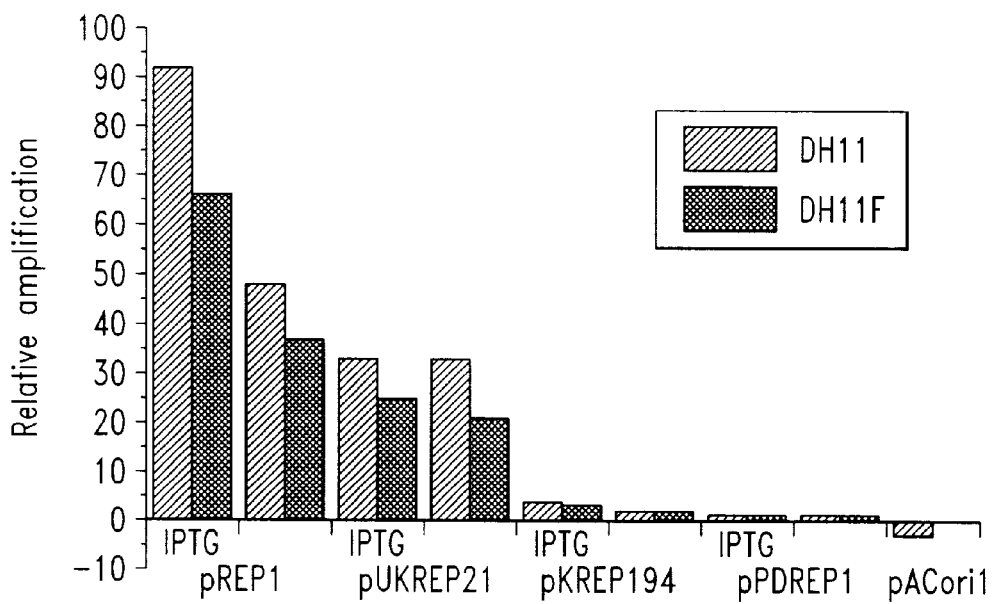

FIG. 11. Relative amplification of pKL1 using different helper plasmids. Helper plasmids pREP1, pUKREP21, pKREP194, pPDREP1 for amplification of the pKL1 copy number and plasmid pACori1 capable of repression of the pKL1 copy number were used. Strains with helper plasmids were also induced with IPTG. The same time strains containing parent plasmids used for construction of helper plasmids and pKL1 were analyzed as well. The ratios of relative copy number of relevant plasmids (parent plasmids and helper plasmids) and pKL1 were measured by gel densitometry. Shown is the relative change of pKL1 copy number in the presence of the relevant helper plasmids or the suppressor plasmid pACori1. In the presence of pPDREP1 pKL1 retained its normal copy number.

Figure 12:
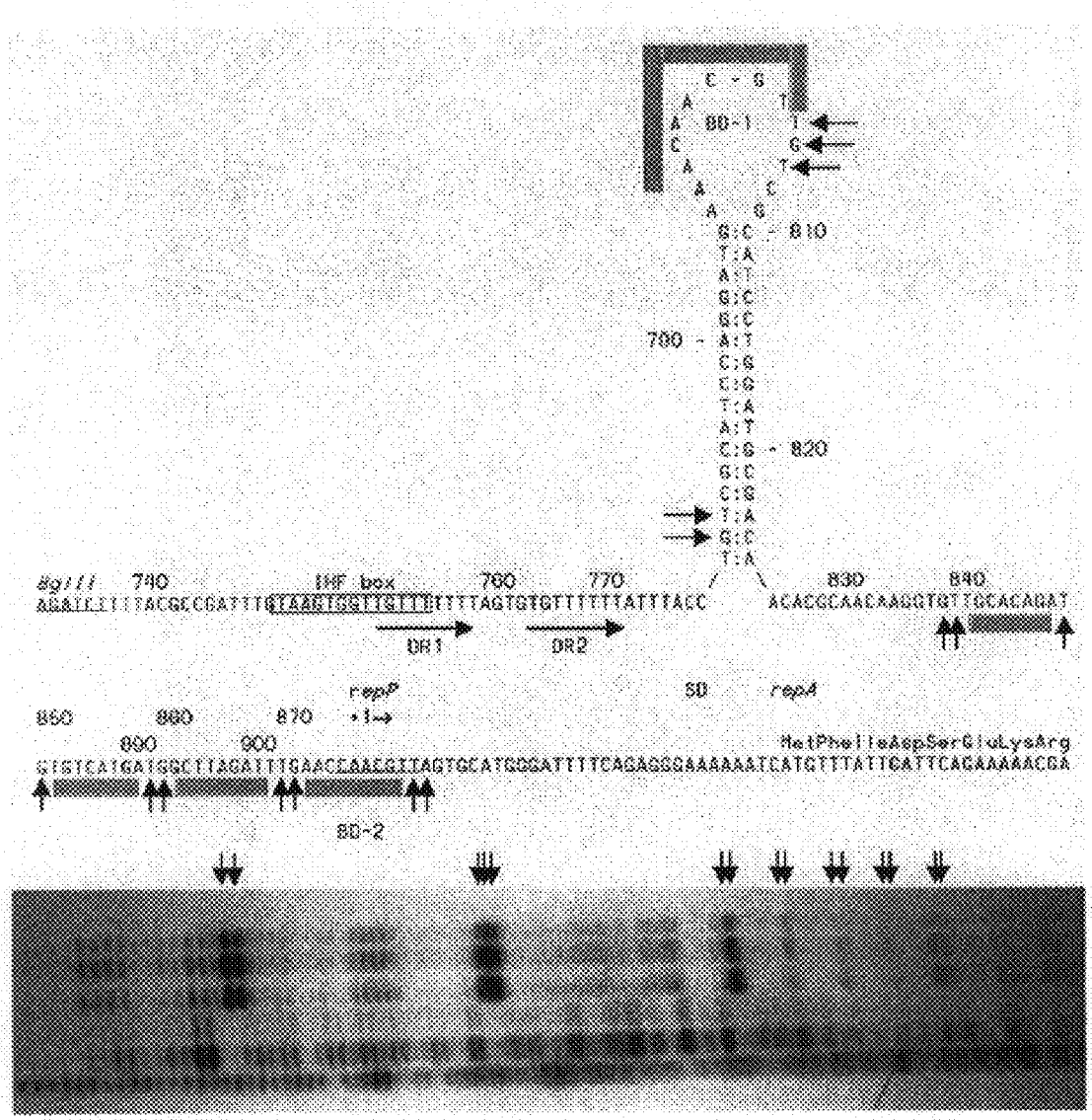

FIG. 12. Analysis of RepA-DNA interactions.

FIG. 12. DNAse I Footprint Assay.

The effect of DNAse I is shown on the DNA sequence; (SEQ ID NO:18) IHF box is IHF binding site, BD-1 and BD-2 are RepA binding sites, +1 is a +1 region of the repA promoter repP, the beginning of repA with its translation (SEQ ID NO:52) is shown as well as ribosome binding site (SD).

An iterative RepA binding is shown as a rectangle: ■
Hot spots of DNAse I activity are shown as arrows: →

Also shown is the actual DNAse I footprint; arrows corresponding to DNAse I hot spots are shown on the DNA sequence above. From the top to bottom lines: the first three lines show the result of DNAse I activity in the presence of RepA; the next two lines show the result of DNAse I activity in the absence of RepA; the bottom line shows chemically hydrolyzed DNA, therefore every nucleotide can be identified. Identical reactions were electrophoresed with a specific DNA sequencing reaction using a specifically designed sequencing primer and this was used to identified RepA binding sites and DNaseI hot spots on the actual pKL1 sequence.

FIG. 12. Gel Retardation Assay with RepA and a Mixture of IHF and RepA.

[$\alpha$-$^{32}$P]-dATP labeled Sau3AI DNA fragment C of pKL1 was incubated with RepA (A) or RepA and IHF (B) to form DNA-protein complexes, which were separated by electrophoresis and examined by autoradiography. (A) lane 1—no protein; lane 2—2 $\mu$M RepA; lane 3—5 $\mu$M RepA; lane 4—8 $\mu$M RepA; lane 5—10 $\mu$M RepA; lane 6—14 $\mu$M RepA. (B) lane 1—no protein; lane 2—2 $\mu$M IHF; lane 3—2 $\mu$M IHF and 0.5 $\mu$M RepA; lane 4—$\mu$M IHF and 1 $\mu$M RepA; lane 5—2 $\mu$M IHF and 3 $\mu$M RepA; lane 6—2 $\mu$M IHF and 6 $\mu$M RepA FIG. 12. Cross-linked RepA Southwestern Assay (Pacific-Southwestern Assay), RepA was cross-linked to different extents (lanes 2–6) using Bis (Sulfosuccinimidyl) suberate and electrophoresed on SDS-PAGE. Samples from an identical gels were blotted onto three nitrocellulose membranes and probed with the specific radiolabeled DNA probes. The probes for Southwestern blots were end-labeled using Klenow fragment and [$\alpha$-$^{32}$P]-dATP.

Panel A—the membrane was probed with a DNA probe containing both RepA binding sites BD-1 and BD-2
Panel B—SDS-PAGE of crosslinked RepA
Panel C—the membrane was probed with a DNA probe containing only BD-1 RepA binding site
Panel D—the membrane was probed with a DNA probe containing only BD-2 RepA binding site.

FIG. 13. DNA sequence of pKL1 (SEQ ID NO:19) and amino acid sequence of RepA (SEQ ID NO:20).

Figure 14:
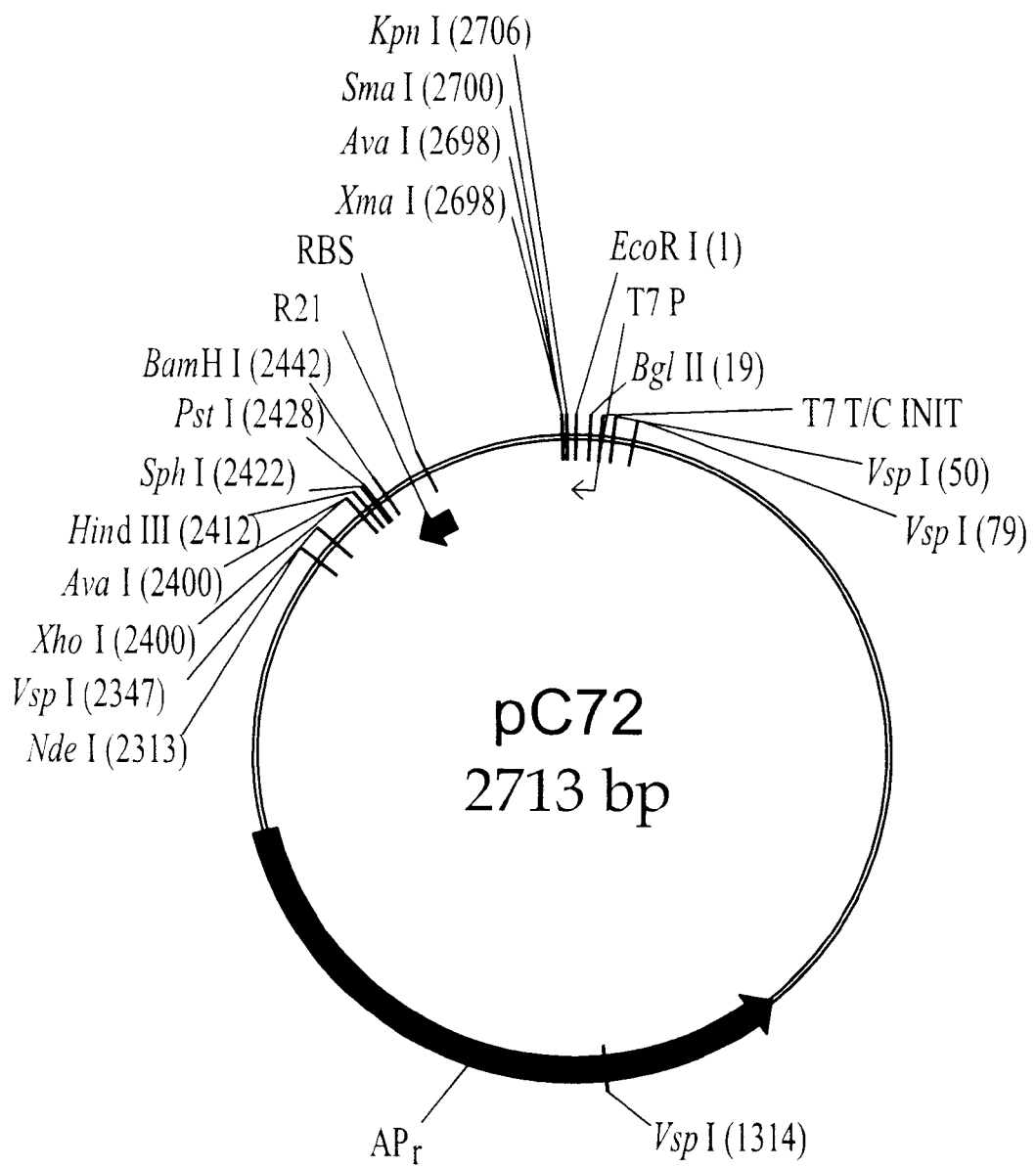

FIG. 14. Map of plasmid pC72. Restriction sites as noted. T7 P is T7 promoter, T7 T/C INIT is +1 region of T7 promoter where m-RNA transcription is initiated, RBS is ribosome binding site of repA gene, R21- beginning of repA open reading frame containing the first 21 codons.

FIGS. 15A–E. Maps of relevant constructs prepared for expression study of MB128 fusion proteins. Map shows only the relevant part for expression of the fusion protein.

FIG. 16. Expression of MBI28 fusion proteins. Whole cell lysates representing expression strains before and after temperature induction were of T7 expression system analyzed by SDS-PAGE. Panel A: lane 1—plasmid free *E. coli* XL1 Blue; lane 2—preinduced XL1 Blue (pGP1-2, pC-2hpro-28); lane 3—induced XL1 Blue (pGP1-2, pR21-2hpro-28); lane 4—induced XL1 Blue (pGP1-2, pC-2hpro-28). Panel B: MW—molecular weight standards—14.4, 21.5, 31, 45, 66.2, 97.4 kDa; lane 1—preinduced XL1 Blue (pGP1-2, pR21-2hpro-28); lane 2—induced XL1 Blue (pGPI-2, pR21-2hpro-28); lane 3—partly purified insoluble fusion protein by Triton X100 wash and organic solvent extraction. Panel C: lane 1—induced XL1 Blue (pGP1-2, pR78-hpro-28); lane 2—induced XL1 Blue (pGP1-2, pR21-2hpro-28).

FIG. 17. Expression and purification of inclusion bodies of fusion proteins R21-2hpro-31 and R21-2hpro-11. Whole cell lysates representing expression strains before and after temperature induction were of T7 expression system analyzed by SDS-PAGE. Fusion proteins were partly purified by Triton X100 and organic solvent extraction. Panel A: MW—relevant molecular weight standards from the bottom—7.3, 19.4, 28.1, 34.2, 50.2 kDa); lane 1—preinduced XL1 Blue (pGP1-2, pR2h-31); lane 3—induced XL1 Blue (pGP1-2, pR2h-31); lane 4—partly purified water insoluble fusion protein by Triton X100 wash; lane 5—previous sample purified by organic solvent extraction. Panel B: lane 1—preinduced XL1 Blue (pGP1-2, pR2h-11); lane 2—induced XL1 Blue (pGP1-2, pR2h-11); lane 3—partly purified fusion protein by Triton X100 wash and organic solvent extraction.

DETAILED DESCRIPTION OF THE INVENTION

In the description that follows, a number of terms are used extensively. The following definitions are provided to facilitate understanding of the invention.

"RepA refers to proteins or polypeptides such as that which is disclosed within FIG. 13, as well as related proteins and polypeptides. Related proteins and polypeptides include analogs or subunits of native proteins or polypeptides that are encoded by nucleotide sequences that hybridize, under stringent conditions, to nucleic acid probes which encode RepA as shown in FIG. 13 (or to their complementary DNA or RNA strands). Further, related proteins or polypeptides may have greater than 70, 75, 80, 85, 90, or 90% homology to the RepA sequence provided in FIG. 13. "Recombinant DNA technology" or "recombinant", as used herein, refers to techniques and processes for producing specific polypeptides from microbial (e.g., bacterial, fungal or yeast) or mammalian cells or organisms (e.g., transgenics) that have been transformed or transfected with cloned or synthetic DNA sequences to enable biosynthesis of heterologous peptides.

A "structural gene" is a nucleotide sequence that is transcribed into messenger RNA (mRNA), which is then translated into a sequence of amino acids characteristic of a specific polypeptide.

An "isolated nucleic acid molecule or protein" is a nucleic acid molecule that is not integrated in the genomic DNA of an organism. One example of an isolated nucleic acid molecule is a chemically-synthesized nucleic acid molecule that is not integrated in the genome of an organism.

The terms "stringent conditions" or "stringent hybridization conditions" refer to conditions under which a test nucleic acid molecule will hybridize to a target reference nucleotide sequence, to a detectably greater degree than other sequences (e.g., at least two-fold over background). Stringent conditions are sequence-dependent and will differ in experimental contexts. For example, longer sequences hybridize specifically at higher temperatures. Generally, stringent conditions are selected to be about 5° C. to about 20° C. lower, and preferably, 5° C. lower, than the thermal melting point (Tm) for the specific target sequence at a defined ionic strength and pH. The Tm is the temperature (under defined ionic strength and pH) at which 50% of a complementary target sequence hybridizes to a perfectly matched probe. Typically, stringent conditions will be those in which the salt concentration is less than about 1.0 M Na ion concentration (or other salts), typically about 0.01 to 1.0 M Na ion concentration (or other salts), at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C.

An "isolated polypeptide" is a polypeptide that is essentially free from contaminating cellular components, such as carbohydrate, lipid, or other proteinaceous impurities associated with the polypeptide in nature. That a particular protein preparation contains an isolated polypeptide can be shown by the appearance of a single band following sodium dodecyl sulfate (SDS)-polyacrylamide gel electrophoresis of the protein preparation and Coomassie Brilliant Blue staining of the gel.

A "fusion protein" is a hybrid protein expressed by a nucleic acid molecule comprising nucleotide sequences of at least two genes. In the context of the present invention, a fusion protein comprises RepA amino acid sequences and additional amino acid sequences. For example, a fusion protein can comprise amino acid sequences of at least part of a RepA protein fused with a polypeptide such as a cationic peptide.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term "expression" refers to the biosynthesis of a gene product. For example, in the case of a structural gene, expression involves transcription of the structural gene into mRNA and the translation of mRNA into one or more polypeptides. In contrast, the expression of a ribozyme gene, discussed below, results in the biosynthesis of a nucleic acid as the end product.

A "vector" is a nucleic acid molecule, such as a plasmid, cosmid, or bacteriophage, that has the capability of replicating autonomously in a host cell. Cloning vectors typically contain one or a small number of restriction endonuclease recognition sites at which foreign nucleotide sequences can be inserted in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

Expression vectors are nucleic acid molecules encoding a gene that is expressed in a host cell. Typically, gene expression is placed under the control of a promoter, and optionally, under the control of at least one regulatory element. Such a gene is said to be "operably linked to" the promoter. Similarly, a regulatory element and a promoter are operably linked if the regulatory element modulates the activity of the promoter. The product of a gene expressed by an expression vector is referred to as an "exogenous" gene product.

A "recombinant host" may be any prokaryotic or eukaryotic cell that contains either a vector. This term also includes those prokaryotic or eukaryotic cells that have been genetically engineered to contain the cloned gene(s) in the chromosome or genome of the host cell.

As noted above, the present invention provides replication genes, an ori region sequence containing the origin of replication and the repA sequence encoding a replication protein RepA necessary for replication, which are used to construct controlled-replication vector systems. In general, these vector systems comprise a repA gene, that encodes RepA protein required for replication, under control of a heterologous promoter, and a replicon unit that is sensitive to the action of the RepA protein in trans.

I. Plasmid Replication

The majority of bacteria contain plasmids; autonomous, self-replicating and normally not essential DNA molecules that are present in defined numbers of copies per cell. Essential functions for the replication of plasmid DNA frequently reside in a relatively small region of the genome. The basic replication regions of plasmids usually contain two essential components—an origin sequence (ori) and at least one gene, usually designated rep, that encodes a protein regulating plasmid replication. Rep proteins may also interact with the host-specified DNA replication apparatus to initiate plasmid replication. Generally, plasmids control their replication such that given steady-state values for their copy numbers are maintained. This is a special type of control, since it requires the genome to measure its concentration continuously and adjust its rate of replication to parallel the rate of growth of the cell mass. Control is exerted through a negative feedback control system. Two basic schemes for the regulation of plasmid replication have been elucidated. In one scheme, the plasmid encodes a small, diffusible RNA molecule that acts as an antisense transcript to repA mRNA. The second basic mechanism is based on a series of direct repeats, designated iterons, that are located within the plasmid origin of replication and are essential for both the initiation of replication and its control. As shown herein, the small cryptic plasmid, pKL1, utilizes a third novel scheme of negative feedback control.

II. Small Cryptic Plasmids

Small cryptic plasmids (SCPs) are extrachromosomal elements that are unusually small and abundant. Although they carry very little genetic information, these plasmids are maintained at high copy numbers. Small plasmids have been described in E. coli, Shigella sonnei, Salmonella enteritidis, Salmonella enterica, Neisseria ghonorrhoeae, Staphylococcus aureus, and Lactobacilli. In particular, SCPs are frequently found in clinical isolates of E. coli. As shown herein, the smallest isolated SCP from clinical E. coli is maintained normally at about 50 copies/host chromosome. Remarkably, this plasmid, called pKL1, is only 1548 bp, merely enough genetic information to replicate itself.

The DNA sequence of a representative SCP, pKL1, was determined. The sequence is presented in FIG. 13. This plasmid encodes a single protein, RepA, which is required for replication, as well as an ori sequence. The ori region comprises an active IHF box (IHF =integration host factor), an oriT homologous sequence, a n'pnmosome assembly signal (n'-pasH). When RepA is provided in trans, a 599 bp fragment (nucleotides 315–894) encompasses a region that can be replicated. This fragment contains the n'-pasH sequence, oriT (origin of conjugative transfer), ori (actual origin of replication, yet unknown), IHF binding site, putative stem-loop structure and two RepA binding sites—BD-1 and BD-2.

Within the context of this invention, the minimal region for replication (minimal replicon) is the region capable of replication when RepA is provided in trans. As shown herein, a 599 bp fragment contains sequences that allows replication. However, this fragment may contain sequences unnecessary for propagation. The minimal region is established by systematic elimination of the various elements in the ori region, inserting the test sequence into an ColE1 type plasmid or ligating the test sequence with a resistance marker, e.g., the kanamycin resistance gene, co-transforming with a vector that expresses RepA, and measuring replication. A polA1 host is used for co-transformation of a heterologous ColE1 type plasmid containing the ori region with a vector that expresses RepA. ColE1 type plasmids are not capable of replication in polA1 host unless they also carry the second functional polA1-independent origin of replication, in this case the minimal replicon of pKL1. The copy numbers of the resulting minimal replicon greatly depends on the concentration of RepA and can be lower or higher than wild type copy number. In addition, under controlled-replication conditions, preferably copy numbers are attained that are equivalent to the copy number of pKL1 under similar conditions. The minimal region for replication may differ from the wild-type sequence by nucleotide changes, insertions, deletions, and the like. However, the minimal region must still be capable of replication.

The minimal region is derived from a small cryptic plasmid, preferably from the same plasmid as RepA is derived from. Minimal regions from small cryptic plasmids are identified as described herein for pKL1. Small cryptic plasmids from bacterial isolates are isolated and analyzed by DNA sequence analysis, restriction digestion or hybridization analysis. DNA sequence analysis will identify open reading frames, especially those with similarity to pKL1 repA gene and motifs characteristic of ori regions. Hybridization of the genome of the small cryptic plasmid with sequences derived from the minimal region of replication and from repA can identify sequences (e.g., restriction fragments) with nucleotide sequence similarity. Preferably, the nucleotide similarity is greater than 75%, 80%, 85%, and 90%. Also preferably, detectable hybridization occurs under normal stringency conditions (5×SSPE, 0.5% SDS, 1×Denhardt's, at 65° C.; or equivalent salt and temperature conditions). A protein called RepA, necessary for plasmid replication, is identified from the DNA sequence of pKL1 and from cloning and expression of the relevant fragment of the small cryptic plasmid pKL1. As used herein, "RepA" refers to the gene product of the repA gene sequence found in small cryptic plasmids. A representative RepA protein from plasmid pKL1 is described herein. RepA proteins from other small cryptic plasmids are within the scope of this invention. Preferably, these proteins have greater than 75%, 80%, 85%, or 90% amino acid identity. In addition, RepA protein used within the present invention may differ from the native protein by amino acid alterations, deletions, insertions, modifications, and the like. However, the RepA protein must still regulate replication of a DNA molecule containing the minimum sequences required for replication. RepA coding sequences may also be identified by hybridization of the repA gene sequence to genomic DNA of small cryptic plasmids. Preferably, detectable hybridization occurs under normal stringency conditions (5×SSPE, 0.5% SDS, 1×Denhardt's, at 65° C.; or equivalent salt and temperature conditions).

III. Vectors

As noted herein, the present invention provides plasmid vectors suitable for expression of heterologous proteins and for amplification of DNA, so called "RAMP" vectors. In particular, these vectors are "controlled-replication" vectors. As used herein, "controlled-replication" vectors are characterized by conditional copy numbers, which vary from low, and can be regulated stepwise to very high values.

"Runaway-replication" plasmids normally control their copy number by small protein repressors at the transcriptional level and antisense RNA that post-transcriptionally regulates the expression of RepA(see, Nordström and Uhlin, Bio/Technology 10:661 (1992)). Plasmid RI is a prototypic example of this class of runaway replication plasmids. These types of runaway replication systems are difficult to control and eventually result in cell death.

In contrast, with small cryptic plasmids, RepA autoregulates its own production. In a representative small cryptic plasmid, pKL1, the RepA protein binds specifically to two binding domains (BD-1 and BD-2) containing 7 bp sequences (CAACGTT) located upstream of repA coding sequence (nucleotides 799-805 and 876-882 in FIG. 13). Binding of RepA to BD-2 is iterative. The consequence of this binding is two-fold: (1) the transcription of repA and hence the production of RepA is down-regulated; and (2) replication of the plasmid is initiated. This upstream region, termed cop (control of plasmid), also contains the promoter repP of RepA, and as such, promotes the replication of the plasmid. Without being held to a particular mechanism of replication, RepA binds to one binding site preferentially as a monomer or dimer and initiates replication of pKL1, and at high enough concentration binds to the second binding site as multimer, possibly a hexamer, and down-regulates transcription of repA gene. Thus, when RepA is in high enough concentration, RepA down-regulates its own production and hence replication of the plasmid slows or ceases. However, when RepA is provided in trans, the high concentration overcomes the titration effect of the down-regulation and controlled-replication ensues. Therefore, repA genes with functional control elements on pKL1 plasmid are likely off and only RepA produced in trans regulates replication. Replication of pKL1 requires functional integration host factor (IHF). The phenomenon of autoregulation of repA together with the absence of iterons and lack of RNA regulation suggests that the regulation of pKL1 replication differs from two so far accepted basic schemes.

As provided herein, a controlled-replication vector system based on small cryptic plasmids is designed such that the repA gene is under control of a heterologous promoter. As used herein, a "heterologous" promoter is any promoter other than the repA promoter that is functional in the host cell and is not regulated by RepA protein. In general, any non-repA promoter that functions in bacterial cells is acceptable. The promoter may be constitutive or inducible; inducible promoters are preferred. Also preferably, an inducible promoter is completely inactive in the absence of the inducer. Typical inducible promoters that may be used within the context of this invention include araB promoter, lac promoter, tac promoter, lambda $P_L$ and $P_R$ promoters, T7 promoter, trpE promoter, T7lac promoter, and the like.

The region for replication is also provided in the vector system. As discussed above, a minimal region is required but additional sequences may be present as long as replication is not affected.

The repA gene and the region for replication may be present on the same or different plasmids. Preferably, they are on separate plasmids. Level of expression of RepA determines copy number of pKL1 or its minimal replicon. The plasmid comprising the repA gene can be a high copy number plasmid with a strong promoter and high levels of expression of RepA, high copy number plasmid with weak promoter and lower level of expression of RepA, low copy number plasmid with strong promoter with moderate to high level of expression of RepA or low copy number plasmid with low expression level is also acceptable. The highest copy number of the plasmid containing the replication region is attained (>2500 copies) when RepA is highly expressed. Moreover, the plasmid comprising the repA gene should be compatible with the SCP ori region.

The plasmid or plasmids of the controlled-replication system optionally comprise additional elements, such as a selectable marker. Suitable selectable markers are well-known and include various drug resistance genes (e.g., kanamycin, ampicillin, chloramphenicol). For expression of a heterologous protein, a cassette comprising a suitable promoter, ribosome binding site, and convenient restriction sites is preferably inserted into the plasmid containing the SCP origin of replication. The choice of promoter depends, at least in part, upon the heterologous protein destined for expression. For example, if the protein is toxic, then a regulated promoter is preferable. The regulated (e.g., inducible) promoter may be the same or different than the promoter controlling repA.

The heterologous protein may be any protein, prokaryotic or eukaryotic in origin. Examples of proteins that are desirable for high expression include cationic peptides (e.g., indolicidin and analogues; for other examples of cationic peptides see U.S. application Ser. Nos. 08/575,052; 08/405,234; 08/614,516; PCT/IB96/0043; 08/460,464; 08/658,857; 08/702,054; 60/002,687; 60/024,754; 60/034,949; and "Methods and compositions for treating infections by administration of cationic peptides and antibiotic agents" filed Mar. 17, 1997), cytokines (e.g., IL-12, IL-2), growth factors (e.g., FGF, PDGF), growth hormones (e.g. human growth hormone), neuropeptides (e.g., CRF, ACTH), and a wide variety of mammalian (e.g., human) proteins or polypeptides (e.g., Factor VIII, or insulin). The protein may be expressed as a fusion protein or as a non-fusion protein. For fusion proteins, the partner peptide may be at the N- or C-terminus, but more usually is at the N-terminus. The partner is typically short in length and may comprise a tag sequence that facilitates purification. Tag sequences are well known in the art and include FLAG, GST, and the like.

The controlled-replication system can be also used to produce large quantities of DNA that are destined for other purposes, such as administration to humans or veterinary animals and birds in the form of a DNA vaccine or even to patients in the form of a prophylactic DNA vaccine. The heterologous gene sequence inserted into the controlled-replication vector typically may include a eukaryotic promoter and other transcriptional elements necessary for functional expression.

IV. RepA Protein

As noted above, the present invention provides RepA protein. For expression and isolation of the RepA protein, the repA gene is placed under control of a strong promoter, such as T7 or tac, in a high copy number plasmid. Merely by way of example, repA is placed under control of the T7 promoter in a plasmid backbone that also contains an ampicillin resistance gene and an f1 ori. This plasmid is called pBGL-R. The plasmid is transformed along with pGP1-2, a vector expressing T7 RNA polymerase under control of lambda promoter, into a suitable host cell, such as XL1 Blue. The cells are induced with IPTG and, following culture, are harvested.

Any one of a variety of standard isolation techniques can isolate RepA protein. Briefly, in one method, harvested cells are lysed in buffer or broken in a French Press homogenizer. RepA protein is initially enriched by precipitation with PEG. The precipitate is collected and resuspended in buffer. Protein is applied to an ion-exchange chromatography column, such as DEAE-cellulose and eluted with a salt gradient. If necessary protein can be further purified using other chromatography columns known to those knowledgeable in art, e.g., heparin-sepharose. Purified protein is analyzed by SDS-PAGE. Preferably, purified protein should display a single band on PAGE by Coomassie blue staining.

V. Preparation of Antibodies against repA

Within one aspect of the present invention, RepA including fragments thereof, may be utilized to prepare antibodies which specifically bind to RepA. Within the context of the present invention the term "antibodies" includes polyclonal antibodies, monoclonal antibodies, fragments thereof such as $F(ab')_2$ and Fab fragments, as well as recombinantly produced binding partners. These binding partners incorporate the variable regions from a gene which encodes a specifically binding monoclonal antibody. Antibodies are defined to be specifically binding if they bind to the RepA with a $K_a$ of greater than or equal to $10^7$ $M^{-1}$. The affinity of a monoclonal antibody or binding partner may be readily determined by one of ordinary skill in the art (see Scatchard, *Ann. N.Y Acad. Sci.* 51:660–672, 1949).

Polyclonal antibodies may be readily generated by one of ordinary skill in the art from a variety of warm-blooded animals such as horses, cows, goats, sheep, dogs, chickens, rabbits, mice, or rats. Briefly, the RepA is utilized to immunize the animal through intraperitoneal, intramuscular, intraocular, or subcutaneous injections. The immunogenicity of a RepA or RepA peptide may be increased through the use of an adjuvant such as Freund's complete or incomplete adjuvant. Following several booster immunizations, small samples of serum are collected and tested for reactivity to the RepA. A variety of assays may be utilized in order to detect antibodies which specifically bind to a RepA. Exemplary assays are described in detail in *Antibodies: A Laboratory Manual*, Harlow and Lane (eds.), Cold Spring Harbor Laboratory Press, 1988. Representative examples of such assays include: Countercurrent Immuno-Electrophoresis (CIEP), Radioimmunoassays, Radioimmunoprecipitations, Enzyme-Linked Immuno-Sorbent Assays (ELISA), Dot Blot assays, Inhibition or Competition assays, and sandwich assays (see U.S. Pat. Nos. 4,376,110 and 4,486,530; see also Antibodies: A Laboratory Manual, supra). Particularly preferred polyclonal antisera will give a signal that is at least three times greater than background. Once the titer of the animal has reached a plateau in terms of its reactivity to the RepA, larger quantities of polyclonal antisera may be readily obtained either by weekly bleedings, or by exsanguinating the animal.

Monoclonal antibodies may also be readily generated using well-known techniques (see U.S. Pat. Nos. RE 32,011, 4,902,614, 4,543,439, and 4,411,993; see also *Monoclonal Antibodies, Hybridomas: A New Dimension in Biological Analyses*, Plenum Press, Kennett, McKeam, and Bechtol (eds.), 1980, and *Antibodies: A Laboratory Manual*, Harlow and Lane (eds.), Cold Spring Harbor Laboratory Press, 1988). Other techniques may also be utilized to construct monoclonal antibodies (see Huse et al., "Generation of a Large Combinational Library of the Immunoglobulin Repertoire in Phage Lambda," *Science* 246:1275–1281, December 1989; see also Sastry et al., "Cloning of the Immunological Repertoire in *Escherichia coli* for Generation of Monoclonal Catalytic Antibodies: Construction of a Heavy Chain Variable Region-Specific cDNA Library," Proc. Natl. Acad. Sci. USA 86:5728–5732, August 1989; see also Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population and utilized to create heavy and light chain immunoglobulin cDNA expression libraries in the λIMMUNOZAP(H) and λIMMUNOZAP(L) vectors. These vectors may be screened individually or co- expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant DNA techniques to incorporate the variable regions of a gene which encodes a specifically binding antibody. The construction of these proteins may be readily accomplished by one of ordinary skill in the art (see Larrick et al., "Polymerase Chain Reaction Using Mixed Primers: Cloning of Human Monoclonal Antibody Variable Region Genes From Single Hybridoma Cells," *Biotechnology* 7:934–938, September 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394-397, 1989; see also, U.S. Pat. No. 5,132,405 entitled "Biosynthetic Antibody Binding Sites"), given the disclosure provided herein.

Once suitable antibodies have been obtained, they may be isolated or purified by many techniques well known to those of ordinary skill in the art (see *Antibodies: A Laboratory Manual*, supra). Suitable techniques include peptide or protein affinity columns, HPLC or RP-HPLC, purification on protein A or protein G columns, or any combination of these techniques. Within the context of the present invention, the term "isolated" as used to define antibodies or binding partners means "substantially free of other blood components." Antibodies of the present invention have many uses. For example, antibodies may be utilized in order to separate fusion proteins having RepA sequences from other cellular constituents.

The following examples are offered by way of illustration, and not by way of limitation.

EXAMPLES

Example 1

General Methods

Bacterial Strains

Clinical strains of *E. coli* and Shigella, Citrobacter, Salmonella and Serratia sp. are obtained from the Hygienic Station (Bratislava, Slovak Republic). Strain identification are performed using Enterotest I and II kits (Lachema Blno, Czech Republic) designed for the differentiation of enteric bacteria. Characterized bacteria strains, bacteriophage, and plasmids that are used herein are presented in Table 1.

TABLE 1

BACTERIAL STRAINS, PLASMIDS AND PHAGES USED IN THIS STUDY.

| Strains/Phages/Plasmids | Description | Source or reference |
|---|---|---|
| *E. coli* strain | | |
| DH1 | recAl endAl gyrA96 thi-1 hsdR17 ($r_k^-$, $m_k^+$) supE44 relA1 | Hanahan (1983) |
| DH11 | DH1 (pKL1) | Burian et al. (1997) |
| JM101 | supE thi-1 Δ(lac-proAB) [F' traD36proAB lacI$^q$ ZΔM15] | Yanish-Perron et al. (1985) |
| KA46 | thr leu pro his thi arg lac gal ara xtl mtl | van Rijn et al. (1989) |
| MN249B | endA1 hsdR17 supE44 thi-1 pcnB | laboratory collection |
| PP3091 | JM101 fis::stm (Sm$^r$) | Spaeny-Dekking et al. (1995) |
| PP1953 | KA46 himD (Tc$^r$) | van Rijn et al. (1989) |
| PP1954 | KA46 himA::tet (Tc$^r$) | van Rijn et al. (1989) |
| PP3291 | KA46 hns::tet (Tc$^r$) | Nora Goosen (unpublished) |
| SF800 | polA1 | laboratory collection |
| XL1 Blue | endA1 hsdR17 ($r_k^-$, $m_k^+$) supE44 thi-1 recA1 gyrA96 relA1 lac [F' traD36 proAB lacI$^q$ ZΔM15 Tn10(TC$^r$)] | Stratagene |
| Bacteriophage | | |
| M13ΔlacI10 | ori$_c$ | Ray et al. (1982) |
| M13ΔlacB1 | ssi n'-pasH | this work |
| M13ΔlacB2 | ssi n'-pasH | this work |
| Plasmid | | |
| pACoril | pSP72 carrying a functional ori of pKL1 | this work |
| pACBGL73 | pACYC184 carrying cop and repA of pKL1 | this work |
| pAClac184 | pACYC184 carrying a translational repA-lacZ fusion | this work |
| pACYC184 | cloning vector Cm$^r$ TC$^r$ | New England Biolabs |
| pB1 | pTZ19R with Sau3AI fragment B of pKL1 cloned in BamHI | this work |
| pB2 | pTZ19R with Sau3AI fragment B of pKL1 in opposite orientation than pB1 | this work |
| pBGL-F | pTZ19R with T7, cop and repA under control of lacP | this work |
| pBGL-R | pTZ19R with T7, lacP, cop and repA in a reverse orientation | Burian et al. (1997) |

TABLE 1-continued

BACTERIAL STRAINS, PLASMIDS AND PHAGES USED IN THIS STUDY.

| Strains/ Phages/ Plasmids | Description | Source or reference |
|---|---|---|
| pBGL73 | pSP73 with T7 promoter, cop and repA of pKL1 | this work |
| pC | pTZ19R with Sau3AI fragment C of pKL1 cloned in BamHI | this work |
| pC72 | pSP72 with EcoRI-BamHI fragment of pC corresponding to Sau3AI fragment C of pKL1 | this work |
| pC72lacTL | pSP72 carrying a translational repA-lacZ fusion | this work |
| pGP1-2 | cI857 Km$^r$ and T7 RNA pol gene under control of P$_L$ promoter | Tabor and Richardson (1985) |
| pGP1261 | IHF binding site from phage Mu genome | van Rijn et al. (1991) |
| pHP45Ω-Cm | Ap$^r$ and Cm$^r$ cassette | Fellay et al. (1987) |
| pK194 | cloning vector Km$^r$ lacP | Jobling and Holmes (1990) |
| pKG1022 | parB Ap$^r$ Kn$^r$ | Gerdes (1988) |
| pKL1 | repA n'-pasH IHF box | Burian et al. (1997) |
| pKL1::Tn1737Km | pKL1 with Tn1737Km | Burian et al. (1997) |
| pKL1Km | pKL1 Km$^r$ | Burian et al. (1997) |
| pKL1Cm | pKL1 Cm$^r$ | this work |
| pKREP194 | pK194 with repA of pKL1 under control of lacP | this work |
| pMMB67EH | RSF1010 replicon Ap$^r$ | Fürste et. al (1986) |
| pORI1 | a fragment of pKL1 from pTZKL1 created by PCR and ligated with Km$^r$ cassette of pKG1022 | this work |
| pOU79 | R1 replicon Ap$^r$ | Larsen et. al (1984) |
| pPD1 | pSP101 replicon T7 and lacP | |
| pPDREP1 | pPD1 with repA of pKL1 under control of lacP | this work |
| pREP1 | pTZ19R with repA of pKL1 under control of lacP | this work |
| pSP72 | cloning vector Ap$^r$ T7 and SP6 promoters | Promega |
| pSP73 | cloning vector, Ap$^r$ T7 and SP6 promoters | Promega |
| pSPori1 | pSP72 carrying a functional ori of pKL1 | this work |
| pSPori2 | pSP72 carrying a minimal functional ori of pKL1 | this work |
| pSPori3 | pSP72 carrying a part of the ori of pKL1 | this work |
| pSPori4 | pSP72 carrying a part of the ori of pKL1 | this work |
| pTZ19R | cloning vector Ap$^r$ T7 and lacP | Pharmacia |
| pTZKL1 | pTZ19R with cloned pKL1 as a EcoRI fragment of pKL1::Tn1737Km | Burian et al. (1997) |
| pUKREP21 | pUK21 with repA of pKL1 under control of lacP | this work |
| pUK21 | cloning vector Km$^r$ lacP with 15% of a wild type activity | Viera and Messing (1991) |

Wild plasmid-containing strains are grown in Luria-Bertani (LB) medium without antibiotics. Minimal inhibitory concentrations (MIC) are measured via the dilution method. Colicin (induction with UV light) and hemolysin (horse blood agar) production are measured as previously described Burian et al., Cs. Epidemiol. 37:329–335 (1988). For selection in integrative incompatibility tests, relevant strains are grown in the presence of ampicillin (Amp, 100 µg/ml), azlocillin (Azl, 50 µg/ml), ticarcillin (Tic, 50 tg/ml), tetracycline (Tet, 15 µg/ml), nalidixic acid (Nal, 50 µg/ml), streptomycin (Stm, 100 µg/ml), kanamycin (Kan, 25 µg/ml) or rifampicin (Rif, 25 µg/ml) as required. For transposition experiments, plasmid pUR887 [pME::Tn1737Km (lacZ), Amp$^r$, Kan$^r$, Tet$^r$, trfAts, tra, incP] (Ubben and Schmitt, Gene 53:127–134 (1987)) is used. Plasmid pHSG415 is used for cotransformation experiments; plasmid pUC4KAPA is used as a source of EcoRI Kan$^r$ cassette.

Strain Manipulations

Bacterial conjugations are carried out in liquid medium. E. coli DHI transconjugants are selected using Nal for selection and Tet, Amp, Azl, or Tic for counterselection. Bacterial transformations are performed via electroporation using a Gene Pulser Apparatus (Bio-Rad) or as described by Hanahan (J. Mol. Biol. 166:557–580 (1983)).

Plasmid Incompatibility and Stability

Integrative incompatibility tests with plasmids pKL7 and pKL5 are performed with a set of standard integrative incompatibility strains according to Sasakawa et al. (Plasmid 3:116–127 (1980)), using a method of conjugation on nitrocellulose filters (0.20 µm HAWP, Millipore) (Yoshida et al., Microbiol. Immunol. 28:63–73 (1984)). Donor strains are E. coli DH1 (pKL7) and E. coli DH1 (pKL7, pKL5). Plasmid stability, including pKL1Km, is determined according to Nordstrom and Aagaard Hansen (Mol. Gen. Genet. 197:1–7 (1984)). Briefly, one colony of a strain containing relevant plasmid is resuspended in LB medium, diluted and plated to give about 500 colonies per plate. Next day the colonies are washed out from the plate, and the cell suspension again diluted and plated. After five passages, the presence of the relevant plasmid is detected by agarose gel electrophoresis of twenty single colonies. One passage is considered to be twenty seven generations.

Plasmid Copy Number and Stability

Measurement of pKL1 copy number is based on the integration of the scan of the photographic negative of an electrophoretogram of plasmids pKL1Km and pBR322 using a Beckman DU65 Spectrophotometer, gel scan accessories and associated software. Plasmids pBR322 and pKL1Km Are isolated from E. coli DH1 (pKL1Km, pBR322). Computation involved ratios of MW and relative amounts of plasmids pKL1 and pBR322 as represented by integrated densitometric peaks. Different himA, himD, hns and fis mutant strains of E. Coli (Table 1) are tested as hosts for plasmid pKL1Cm. Bacterial transformations are performed via electroporation using a Gene Pulser Apparatus (Bio-Rad) and corresponding protocol.

Plasmid Purification and Quantification

Plasmids are isolated by a rapid alkaline lysis procedure. Electrophoresis is performed in 1% agarose gel and TBE buffer for 2 h at 5 V cm$^{-1}$. After electrophoresis, gels are stained in 1 µg/ml ethidium bromide for 1 h and photographed under 254 nm UV irradiation. Relative plasmid ratios in E. coli KL4 are computed on the basis of spectrophotometer scanning of the photographic negatives of agarose gels using a Beckman DU65 Spectrophotometer, gel scanning accessories and associated software. Computations are based on ratios of molecular weight and relative amounts of plasmids represented by areas of densitometric peaks. For comparison, the relative copy number of the plasmid pKL7 was set equal to one.

Plasmid Measurement

The size of plasmids pKL1, pKL2, pKL3 and pKL5 are computed from the electrophoretic mobility of standard plasmids using the program GraphPad (ISI, USA). The square of the correlation coefficient of the calibration line is 0.9996. The length of all plasmids, except pKL7, are also measured by electromicrograms. The size of pKL7 (48.53 kb) is obtained graphically by extrapolation using plasmid standards and the program GraphPad. The square of the correlation coefficient of the calibration line is 0.9984.

Transposition

Bacterial conjugation of the transposon vector from *E. coli* JM106 (pUR887) to *E. coli* MC4100 (pKL1) is carried out on solid media. Selection of transconjugants is done in the presence of Stm and Kan at 30° C. This results in the selection of cells with the transposon integrated into either the bacterial chromosome, the resident plasmid pKL1 or generally transconjugants harboring the temperature-sensitive plasmid pUR887. Several transconjugants are washed out of the plate with LB and transferred to the 100 ml of LB media with Kan and incubated at 42° C. overnight. The final selection of Tn1737Km insertions into pKL1 is then accomplished by the transformation of plasmid free recipient cells *E. coli* DH1 with isolated pDNA and transformants selected for Kan$^r$. Plasmid DNA is then isolated from twenty transformants and analyzed by agarose gel (1%) electrophoresis.

Topolisomerase I Assay

Plasmid DNA (pDNA) is purified in CsCl gradients by ultracentrifugation. The enzyme reaction (20 $\mu$l) contains 0.1–0.5 $\mu$g of pDNA in 20 mM Tris-HCl (pH 7.6), 100 mM NaCl, 1 mM EDTA, 100 $\mu$g/ml BSA and 1 U of topoisomerase I and is incubated for one hour at room temperature.

Electron Microscopy

Samples for electron microscopy are deproteinized with a mixture of chloroform:isoamyl alcohol (24:1) and precipitated by the addition of ethanol. Electron microscopy is performed on copper grids with Parlodion membranes (Fluka, Germany) via the cytochrome c/water method (Bukhard and Puhler, in: J. Grinsted and P. M. Bennett (Eds.), *Methods in Microbiology, Plasmid Technology 2nd Edition*, Academic Press, London, pp. 155–177, 1988). Samples are doubly contrasted in uranyl acetate (30 s) and by vacuum evaporation of a mixture of platinum and palladium (80:20) in a Balzers BAE 080 apparatus (Balzers, Switzerland) and observed with Tesla 50OBS (Tesla Brno, Czech Republic) electron microscope at 80 eV.

β-Galactosidase Enzyme Activity

Cells grown in LB medium overnight are inoculated (2%) into fresh, prewarmed medium and grown to 1.5 OD$_{600}$. A 100 $\mu$l aliquot is added to 900 $\mu$l of Z buffer (Miller, *Experiments in Molecular Genetics*, New York: Cold Spring Harbor, 1972) with 5 mg/ml of lysozyme. The cells are incubated for 15 min at 20° C., followed by the addition of 10 $\mu$l of 0.1% SDS. The suspension is briefly vortexed and incubated for 5 min at RT. The cell suspension is then diluted and 1.5 ml is mixed with 0.5 ml ONPG (4 mg l$^{-1}$) in a spectrophotometer cuvette. Reactions are monitored at 28° C. using a Beckman DU65 Spectrophotometer, cuvette transport accessories and kinetic module.

DNA Manipulations

Restriction endonucleases and T4 DNA ligase were purchased from Pharmacia Biochemicals and used according to manufacturer's recommendations. Southern hybridization is performed on Hybond membrane (Amersham) using the VacuGene (Pharmacia Biotech.) for vacuum DNA blotting from agarose gel, Rapid Hybridization Kit (Amersham), 10 $\mu$Ci [$\alpha^{32}$P]-dATP (Amersham) according to standard protocols.

DNA Sequencing and Computer Analysis

The DNA sequence of both strands of relevant pKL1 DNA fragments is determined using an Applied Biosystems model 373A automated DNA sequencer and the associated reagents, protocols, and software (version 1.10) for dye primer cycle sequencing (ABI). Partial sequences are aligned to form a pKL1 DNA sequence by the program DNASIS (Pharmacia). The analysis of the DNA sequence for open reading frames, coding regions, translation signals, gene translation, protein hydropathy index and secondary structure predictions of RepA was performed using PC-Gene software version 6.70 (IntelliGenetics). The DNA sequences of pKL1 and RepA are compared with NCBI databases using the BLAST family of programs (Altschul et al., *J. Mol. Biol.* 215:403–410 (1990)).

Southwestern Analysis

A lysate of thermoinduced *E. coli* XL1 Blue (pBGL-R, pGP1-2) and purified protein are resolved by SDS-PAGE and blotted onto a nitrocellulose membrane (12 volts, 36 min, Transblot apparatus LKB). Membranes are blocked with 5% nonfat dry skim milk, 10% glycerol, 2.5% Nonidet P-40, 0.1 mM DTT and 150 mM NaCl in 10 mM Tris-HCl (pH 7.6) three times (30 min) at 23° C. After blocking, the membrane is briefly rinsed in buffer containing 10 mM Tris-HCl (pH 7.6), 40 mM NaCl, 1 mM EDTA, 1 mM DTT, 8% glycerol and 0.125% nonfat dry skim milk. The membrane is incubated for 1.5 h in a sealed plastic bag with 3 ml binding buffer containing the radiolabeled probe, 5 mM MgCl$_2$ and 20 $\mu$g of briefly sonicated bacterial chromosomal DNA as carrier. Fragments are excised from plasmid pTZKL1 with EcoRI or plasmid pC with EcoRI and BamHI and end-labeled with Klenow polymerase in the presence of 10 $\mu$Ci [$\alpha^{32}$P]-dATP (Amersham) and 200 $\mu$M dCTP, dGTP and dTTP in One Phor All Buffer (OPA) (Pharmacia Biochemicals). The results are recorded by autoradiography.

Pacific-Southwestern Analysis

Purified RepA protein was cross-linked using Bis (Sulfosuccinimidyl)suberate (Pierce) according to manufacturer instructions. Samples were then electrophoresed on SDS-PAGE, blotted onto a nitrocellulose membrane and processed as was described above (Southwestern analysis). Different [$^{32}$P]labeled DNA probes containing RepA binding sites were prepared and used for analysis.

Construction of pKL1 Derivatives

A plasmid, pKL1::Tn1737Km, harboring the transposon in a non-essential region is isolated. The transposon is excised from pKL1::Tn1737Km by EcoRI digestion, which cuts the transposon close to both ends. A gene cassette encoding Km$^r$ is ligated to the EcoRI fragment to create plasmid pKL1Km. The Km$^r$ cassette is subsequently replaced with a EcoRI Cm$^r$ gene cassette of pHP45Ω-Cm (Fellay et al., *Gene* 52:147–154 (1987)), creating pKL1Cm.

The Tn1737Km is integrated into the palindromic sequence "AGCG!CT" of plasmid pKL1; the exact site of the insertion is marked (!). The residual sequence of Tn1737Km in both pKL1Km and pKL1Cm is: GGGGAAC-CCCA<u>GAATTC</u>TGCGGGCTCCC (SEQ ID NO:21) (EcoRI site is underlined). The copy number of pKL1Km is 47 copies per chromosome using compatible pBR322 as the internal standard. pKL1 Cm is used for further testing of the replicon in different mutant host strains of *E. coli*.

Examples of Construction of Recombinant Plasmids and Phases

Plasmid pKL1::Tn1737Km (Table 1) is cleaved with EcoRI and the four restriction fragments separated by agarose gel electrophoresis. The fragment corresponding to the linear plasmid pKL1, but with EcoRI ends, is identified by Southern hybridization. The relevant DNA fragment of pKL1 is electroeluted from the agarose gel using an Extraphor apparatus (LKB) and ligated with an EcoRI kanamycin gene cassette of plasmid pUC4Kappa (Pharmacia) and the EcoRI chloramphenicol gene cassette of plasmid pHP45Ω-Cm (Fellay et al., *Gene* 52:147–54 (1987)) to create plasmids pKL1Km and pKL1 Cm.

Restriction endonuclease Sau3AI is used to generate the DNA fragments of pKL1. Four of the five Sau3AI fragments are cloned into BamHI site of the pTZ19R resulting in recombinant plasmids pA, pB I, pB2 (opposite orientation of the Sau3AI fragment B), pC and pD. Plasmid pTZKL1 results from ligation of EcoRI linearized pTZ19R and EcoRI fragment corresponding to the pKL1 part of plasmid pKL1Km. Plasmid pTZKL1 is used for the generation of SphI-SphI and BglII-BamHI fragments containing pKL1 DNA sequences. Relevant fragments are cloned to the SphI and BamHI sites respectively of the pTZ19R resulting plasmids pBGL-R, pBGL-F and pSPH-F (R and F are orientations of the cloned fragment in the sense of the reverse (R) or forward (F) sequencing primers of pTZ19R).

The EcoRI-BamHI fragment of the plasmid pC containing Sau3AI fragment C of pKL1 is recloned to vectors pSP72 and pSP73 respectively, resulting in plasmids pC72 and pC73. The BglII-EcoRI fragment of plasmid pTZKL1 is cloned to the BamHI and EcoRI sites of vector pSP73 resulting in plasmid pBGL73. Plasmid pREPI is the result of cloning the amplified PCR fragment of pTZKL1 containing the repA gene without its promoter. The amplification primers,

GATTGGATCCAACGTTAGTGC (SEQ ID NO:22)
GCCAAGATCTAATACGACTCAC (SEQ ID NO:23)

are synthesized using the 391 DNA Synthesizer (ABI) and associated reagents. The products of five 10 µl amplification reactions are purified using a Sephaglass BandPrep Kit (Pharmacia), eluted with 20 µl of dH$_2$O and cleaved with 50 U EcoRI and 50 U BamHI in 100 µl reaction volume with 1×OPA buffer (Pharmacia) at 37° C. for two hours. The resulting EcoRI-BamHI fragment is ligated between the EcoRI and BamHI sites of pTZ19R, resulting in plasmid pREP1. The same fragment is recloned from pREP1 to the vector pSP73, resulting in pREP73.

The BamHI fragment of pKL1::Tn1737Km carrying a promoter-less lacZ gene, is cloned into the BamHI site of pC72. Blue colonies on LB plates with X-gal and Ap harbor pC72lacTC.

A fragment containing the ori region of pKL1, amplified from pTZKL1 using the primers:

CCCTCTGAGGATCCCATGCACTAACG & (SEQ ID NO:24)
GCCAAGATCTAATACGACTCAC (SEQ ID NO:23)

is digested with BamHI and EcoRI. The resulting fragment is ligated with the BamHI-EcoRI fragment from pKG1022 that contains Km$^r$ gene. *E. coli* XL1 Blue containing pREP1 is transformed with 2 µl of the ligation mixture and transformants containing plasmids pREPI and pORI are selected on LB with kanamycin. The same amplified product is digested with BglII and EcoRI and also ligated with a DNA fragment containing the Km$_r$ gene resulting in pORIΔinc.

Plaque Morphology Assay

Plasmids pB1 and pB2 are digested with EcoRI and HindIII. The resulting DNA fragments, B1 and B2, are identical, except for the reverse orientation of EcoRI and HindIII. These two DNA fragments are inserted between the EcoRI and HindIII sites of the filamentous phage M13Δlac110 to produce phages M13ΔlacB1 and M13ΔlacB2. A culture of *E. coli* XL1 Blue with a cell density about 0.5×10$^8$ cells per ml is infected overnight (0.1 multiplicity of infection) with M13Δlac110, M13ΔlacB1 and M13ΔlacB2 respectively. Cells are pelleted, and a series of diluted phage stocks are then used for the determination of phage titers and plaque diameters.

Expression of RepA in a T7 Promoter System

*E. coli* XL1 Blue containing the expression plasmid of interest, as well as pGP1-2, are cultivated at 28° C. with vigorous shaking overnight in T-broth. An equal volume of fresh prewarmed medium is added and the temperature raised to 42° C. for two hours. Cells are harvested by centrifugation, lysed in Laemli's sample buffer by boiling for 5 min and analyzed by SDS-PAGE (4% stacking; 15% separating gels) and Coomassie blue staining according to standard protocols. Dried gels are scanned using a Beckman DU-65 Spectrophotometer, gel scan accessories and associated software.

Gel Retardation Assays

DNA fragments are labeled using Klenow fragment and [α-$^{32}$P]-dATP as above. The binding assay is performed with a 302 bp EcoRI-HindIII fragment from pC containing a putative IHF box of pKL1 and an 180 bp HindIII fragment from pGP1261 containing the phage Mu IHF box (van Rijn et al. *Nucl Acids Res* 19:2825–2834 (1991)). IHF or RepA protein is diluted in 50 mM Tris-HCl pH 7.5, 1 mM EDTA, 10% glycerol and freshly added 10 mM 2-ME. Labeled DNA fragments are incubated with 50 pmol and 100 pmol of IHF at 0° C. for 20 min in buffer containing 50 mM Tris-HCl pH 8.0, 0.1 mg/ml BSA, 1 mM DTT and 75 mM KCl. Samples are analyzed on a 5% polyacrylamide gel in TBE run at 7–8 mA per gel for 1 hour at 4° C. Gels are dried on Whatman paper and the results visualized by autoradiography.

Example 2

Identification and Isolation of Strains Containing Small Cryptic Plasmids

Clinical strains of *E. coli* are isolated from patients with urogenital infections. Many of these strains harbor low molecular weight plasmids. An example of electrophoretic plasmid profiles of clinical *E. coli* strains harboring low MW plasmids is shown in FIG. 1. As shown, as many as eight of 15 randomly chosen clinical strains carry small cryptic plasmids (SCPs) (1.5–4 kb) (FIG. 1, lanes 1, 2, 4, 5, 9, 10, 14 and 15). Two of the strains appear to harbor SCPs exclusively (FIG. 1, lanes 14 and 15).

One of these typical multi-plasmid *E. coli* strains that harbors SCPs, KL4 (FIG. 1, lane 1), is selected for further study. Three different approaches are used to resolve the plasmids in KL4: (1) the analysis of relaxation of covalently closed circle forms via the activity of topoisomerase I; (2) the direct visualization of relaxed total plasmid DNA by electron microscopy; and (3) the analysis of plasmid profiles of transconjugants and transformants of *E. coli* strain DH1.

Figure 2:
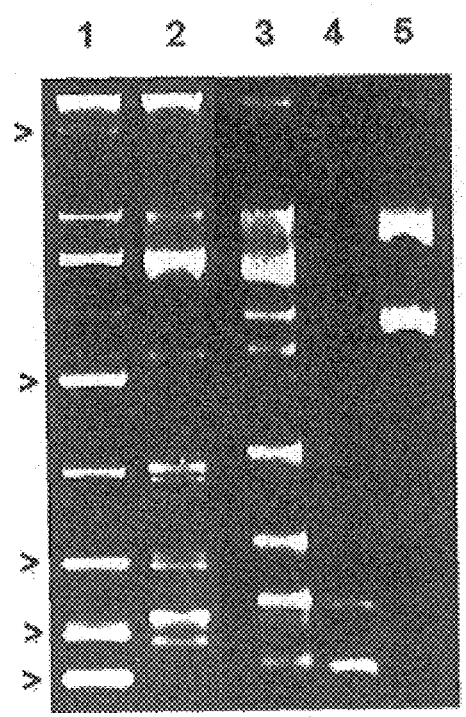
FIG. 2. Topoisomerase I analysis of plasmids of E. coli KL4 and transposition of pKL1 by Tn1737Km. Lanes 1 and 3 contain total plasmid DNA isolated from E. coli KL4. CCC forms of plasmids (lane 1) are marked (>) according to result of topoisomerase I analysis (lane 2). Lane 4 contains plasmid pKL1 isolated from E. coli DH11. Lane 5 contains plasmid pKL1::Tn1737Km.

Topoisomerase I allows identification of covalently closed circle (CCC) forms and open forms of plasmids by altering the CCC form of plasmid DNA (pDNA) to a relaxed open circle (ROC) form, which has different electrophoretic mobility. In KL4, it is possible to assign electrophoretic bands corresponding to particular CCC forms of five distinct plasmids. Following the action of topoisomerase I, newly appearing ROC forms are clearly visible and CCC forms are absent by electrophoretic analysis. This is particularly obvious for plasmids pKL1 and pKL5 (FIG. 2, lanes 1 and 2). Some of the multiple topoisomer states between CCC and ROC forms are also visible. In addition, the ROC form of the large plasmid pKL7 is visualized at the top of the agarose gel.

Figures 3A, 3B:
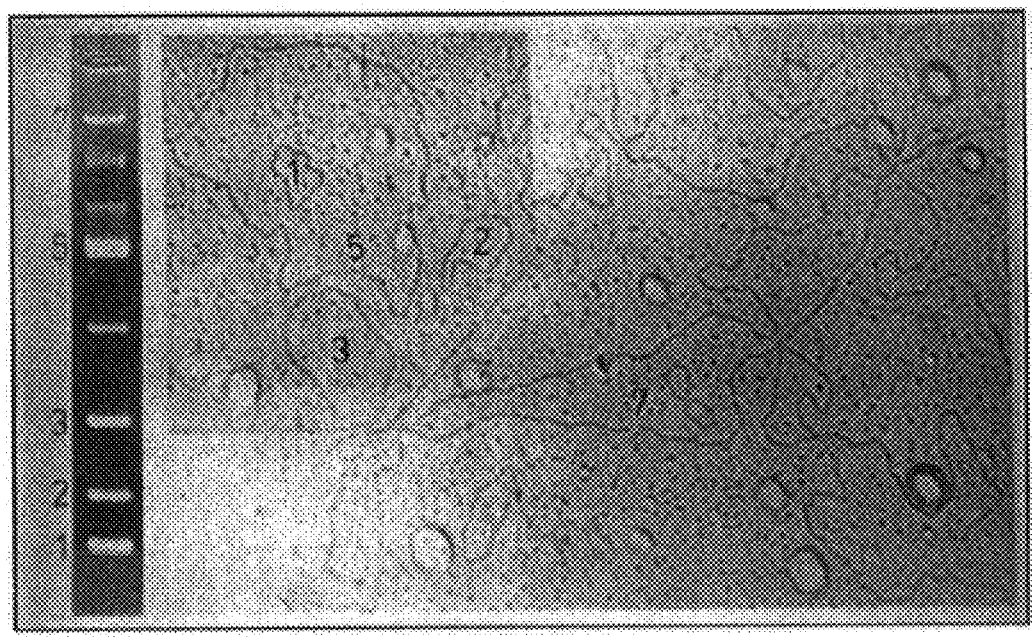
FIGS. 3A and B. Electron microscopy and electrophoresis of total plasmid DNA of E. coli KL4. Plasmid DNA isolated from E. coli KL4 was analyzed by agarose gel electrophoresis (A) and electron microscopy (B). Plasmid DNA for EM was treated with topoisomerase I. Plasmids were identified according to electrophoretic mobility and by direct measurement of DNA length on the photograph as pKL1 (1), pKL2 (2), pKL3 (3), pKL5 (5) and pKL7 (7).

Isolated total plasmid DNA treated with DNA topoisomerase I is analyzed by electron microscopy (EM). As seen in FIGS. 3A and 3B, five ROC that are different sizes are observed by EM (FIG. 3B), and the corresponding plasmids are also displayed on an agarose gel (FIG. 3A).

E. coli KL4 is readily conjugable. The minimum inhibitory concentration (MIC) for 26 antibiotics and chemotherapeutics determined for E. coli KL4 revealed resistance to several antibiotics, Amp (>128 µg/ml), Azl (>128 µg/ml), Tic (>256 µg/ml) and Tet (128 µg/ml). The production of colicin or hemolysin is not detected. Some transconjugants selected for $Tet^r$ are also resistant to the β-lactam antibiotics Amp, Azl and Tic. By electrophoretic analysis, a large plasmid, pKL7 (48.53 kb), is present in all $Tet^r$ transconjugants; in some instances, the plasmid pKL5 (8.3 kb) is also present. Moreover, all transconjugants selected on one of the β-lactam antibiotics are $Tet^r$ and harbor both pKL7 and pKL5. Occasionally, Tet and Amp selected transconjugants also contain the SCP, pKL3 (3.2 kb). Taken together, these results indicate the presence of five quite distinct plasmids in E. coli KL4, three of which are SCPs.

Strains of DH1 that contain only one of the plasmids present in KL4 are isolated. DH1 (pKL7) is isolated from transconjugants selected on Tet containing media; DH1 (pKL5) is selected Amp-containing media after transformation of E. coli DH1 with plasmid pKL5. Single plasmid-containing strains harboring either pKL3, pKL2, or pKL1 SCPs are similarly prepared via cotransformation with plasmid pHSG415 (ratio 1:1000 with the SCPs). About 10%–20% of the transformants are found to host two plasmids. pHSG415 has a thermosensitive replicon, thus transformants are cultivated at 28° C., and plasmid pHSG415 is cured from the transformants by cultivation at 42° C.

Example 3

Characterization of Small Cryptic Plasmids

Plasmid Properties

All plasmids are examined for mobilization by pKL7, the occurrence of resistance genes as well as stability, and plasmids pKL5 and pKL7 are further examined for incompatibility. An integrative incompatibility test using liquid mating developed by Sasakawa et al. (*Plasmid* 3:116–127 (1980)) compares the relative mating frequency of a donor carrying a test plasmid with that of recA recipients carrying various integrated plasmids. The mating frequency of an incompatible plasmid should be at least two fold lower than of a compatible plasmid. Accordingly, pKL5 and pKL7 belong to incIc and incT respectively. Plasmids pKL1, pKL2 and pKL3 are compatible with all plasmids used in this study—pHSG415 (PSC101 replicon), pTZ19R (ColE1 replicon) and F. The presence of SCPs had no apparent influence on the resistance phenotypes of transconjugants or transformants. The basic features of these plasmids are summarized in Table 2.

TABLE 2

| Plasmid | MW[kb][a]EL/EM | RCN[b] | Inc[c] | Con/Mob[d] | Resistance |
|---|---|---|---|---|---|
| pKL7 | *>40 | 01 | incT | +/+[e] | Tet |
| pKL5 | 8.27/8.30 ± 0.09 | 24 | incIa | −/+ | Amp, Azl, Tic |

TABLE 2-continued

| Plasmid | MW[kb][a]EL/EM | RCN[b] | Inc[c] | Con/Mob[d] | Resistance |
|---|---|---|---|---|---|
| pKL3 | 3.17/3.05 ± 0.05 | 52 | nd | −/+ | — |
| pKL2 | 2.16/2.12 ± 0.06 | 34 | nd | −/− | — |
| pKL1 | 1.63/1.51 ± 0.06 | 83 | nd | −/± | — |

[a]MW - molecular weight found by electrophoresis/electron microscopy (EL/EM)
*MW of pKL7 was determined only by electrophoresis
[b]RCN - relative copy number is the ratio of copy number of plasmids pKL1, pKL2, pKL3 and pKL5 to plasmid pKL7 (pKL7 relative copy number = 1)
[c]Inc - incompatibility groups
[d]Con/Mob - conjugation and/or mobilization of a plasmid
[e]plasmid pKL7 is conjugable and can also mobilize other plasmids
±- mobilization of plasmid pKL1 by plasmid pKL7 was found to be infrequent by conjugation on nitrocellulose filters
[e]nd - unable to define the Inc group Non-Essential Region A region of pKL1 that is non-essential for the replication of the plasmid is identified by transposition. The transposition of Tn1737Km to the smallest of the SCPs in KL4, pKL1, yields several clones harboring the 11.3 kb plasmid (FIG. 2, lane 5). Restriction analysis with EcoRI indicates that these plasmids are in vivo recombinant plasmids, pKL1::Tn1737Km. The transposon Tn1737Km also contains a promoter-less lacZ gene suitable for transcriptional fusions. Analysis of 44 isolates of XL1 Blue (pKL1::Tn1737Km) shows expression of β-galactosidase activity ranging from 85 to 635 Miller Units (Miller, supra). For comparison, using IPTG, a fully induced E. coli strain grown on glucose has approximately 1000 Miller Units. In contrast, XL1 Blue does not express measurable β-galactosidase activity. Thus, in these transposed bacteria, Tn1737Km transposes into pKL1 at a non-essential region for replication. Furthermore, the variable enzyme activity suggests that transposition occurs at different locations and/or orientations. Restriction analyses of these transposed pKL1::Tn1737Km plasmids localizes a nonessential region for replication of pKL1 between the HaeIII and SphI restriction sites in pKL1.

The stability of 18 clones containing pKL1::Tn1737Km and expressing different levels of β-galactosidase activity are comparably stable to pKL1 for at least 135 generations.

Lack of Requirement of polA for Replication

Plasmid pKL1::Tn1737Km is cleaved with EcoRI into four fragments that are separated by agarose gel electrophoresis. The EcoRI sites in Tn1737Km are located close to both ends leaving only 28 nucleotides remaining after excision of the transposon. The fragment corresponding to the linear plasmid pKL1 with EcoRI ends is identified by Southern hybridization. This fragment is subsequently isolated from a gel by electroelution and ligated to an EcoRI kanamycin gene cassette from plasmid pUC4KAPA, creating plasmid pKL1Km. Plasmid pTZKL1, which is pTZ19R containing the pKL1 fragment, is prepared as well. Surprisingly, the EcoRI KL1 insert is found in only one orientation. Several kanamycin-sensitive clinical strains of Shigella, Citrobacter, Salmonella and Serratia sp. are successfully transformed by pKL1Km.

Plasmids pKL1Km and pTZKL1 are used to test whether the pKLI replicon requires polA for replication. A polA1 mutant strain of E. coli, SF800 (pola 1), is transformed with pKL1Km, pTZKL1, or pTZ19R. As expected, pTZ19R does not replicate in this host. However, both pKL1 and pTZKL1 replicate and are stable, suggesting that polA is not required for replication.

Gene Products

Figures 4A, 4B, 4C, 4D:
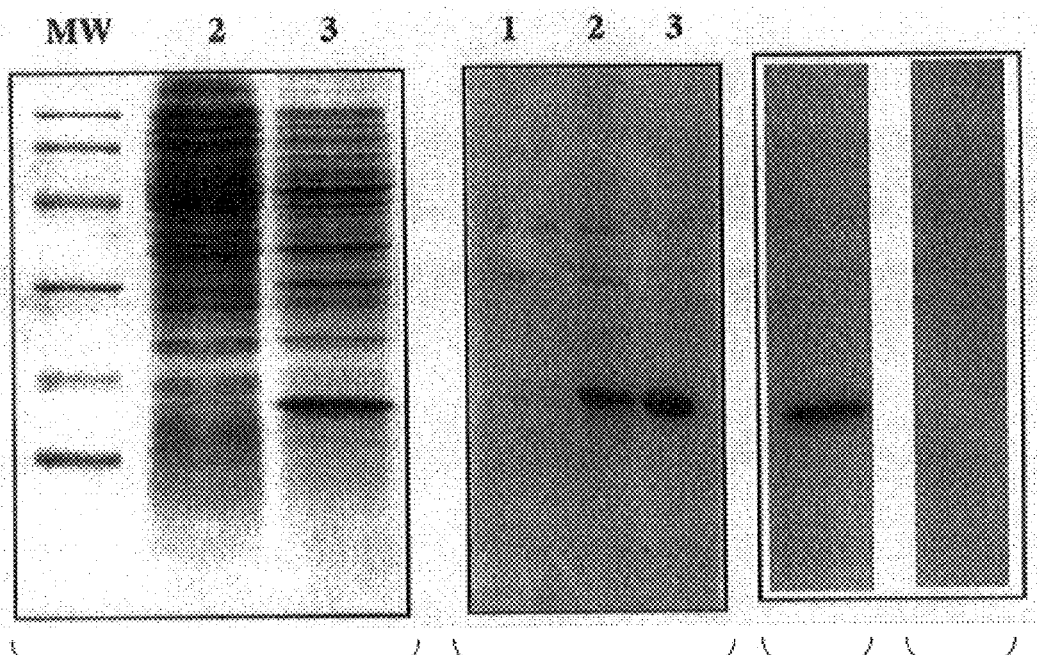
FIGS. 4A, B, C, and D. Southwestern analysis of RepA. Panel A—Whole cell lysates representing an expression strain before and after temperature induction were analyzed by SDS-PAGE. Samples from an identical gel were blotted onto nitrocellulose membranes and probed with the labeled pKL1 DNA probes. The probes for southwestern blots were end-labeled using Klenow fragment and [$\alpha$-$^{32}$P]-dATP. Molecular weight standards are as noted. Panel A: Standard proteins (MW); E. coli XL1 Blue cells cultivated at 37° C. (lane 1); E. coli XL1 Blue cells containing pGP1-2 and pBGL-R cultivated at 30° C. and shifted to 42° C. for 2 h (lane 2). Panel B: Southwestern blot of E. coli XL1 Blue cells cultivated at 37° C. (lane 1); E. coli XL1 Blue cells containing pGP1-2 and pBGL-R cultivated at 30° C. and shifted to 42° C. for 2 h (lane 2); purified RepA protein (lane 3). Panels C & D: Whole cell lysates of E. coli XL1 Blue cells containing pGP1-2 and pBGL-R cultivated at 30° C. and shifted to 42° C. for 2h were blotted onto nitrocellulose membrane and probed with the labeled pKL1 probes: BglII-BamHI fragment of pTZKL1 (panel C) and with the labeled EcoRI-XbaI fragment of pDBGL.

The plasmid pTZKL1 is further examined for production of gene products expressed from the T7 promoter. A pTZKL1 transformant is co-transfected with pGP1-2 that has the T7 RNA polymerase gene under control of the $\lambda_L$ promoter and cI857. No expression is detected. However, when pBGL-R, a construct of pTZ19R containing a BglII-BamHI fragment of pTZKL1 (FIG. 6), is tested for expression after co-transfection with pGP1-2, a protein with a molecular mass of approximately 17.5–17.9 kDa is clearly detected (FIG. 4, panel A). The difference in expression between the two plasmids may be due to orientation of pKL1 sequence: the orientation of the BglII-BamHI fragment in pBGL-R is opposite to its orientation in pTZKL1. The protein, called RepA, is resolved by SDS-PAGE, and electrophoretically transferred to an Immobilon PVDF membrane (Millipore Canada Ltd.) for isolation and direct N-terminal amino acid analysis.

Example 4

DNA Sequence Analysis of pKL1

The DNA sequence of both strands of pKL1 DNA is determined and presented in FIG. 13. The plasmid is 1548 bp. A DNA computer analysis of the complete pKL1 DNA sequence (Fickett, *Nucl. Acids Res.* 10:5303–5318 (1982); Kolaskar and Reddy, *Nucl. Acids Res.* 13:185–194 (1985)) suggests a single open reading frame, a 473 bp coding region $ORF_{913-1386}$ on the heavy DNA strand (H strand) of pKL1. The beginning of the DNA sequence of $ORF_{913-1386}$ corresponds to the 48 known amino acids of the RepA protein sequence. The complete sequence of RepA is deduced from the pKL1 DNA sequence and is presented in FIG. 13. The molecular weight of RepA is 17960 (158 aa).

Analysis of the H and light (L) DNA strands of pKL1 indicated a low probability of other potential protein coding regions. Although there are several open reading frames (ORF) that are greater than 50 codons, only $ORF_{913-1386}$ is adjacent to a typical *E. coli* ribosome binding site (RBS). Furthermore, all the other ORFs can tolerate insertion of the transposon Tn1737Km, thus they either do not encode a protein or do not encode a protein necessary for plasmid replication. Moreover, T7 expression experiments described above support the conclusion that pKL1 encodes only one protein, RepA, the product of the repA gene.

Figure 7:
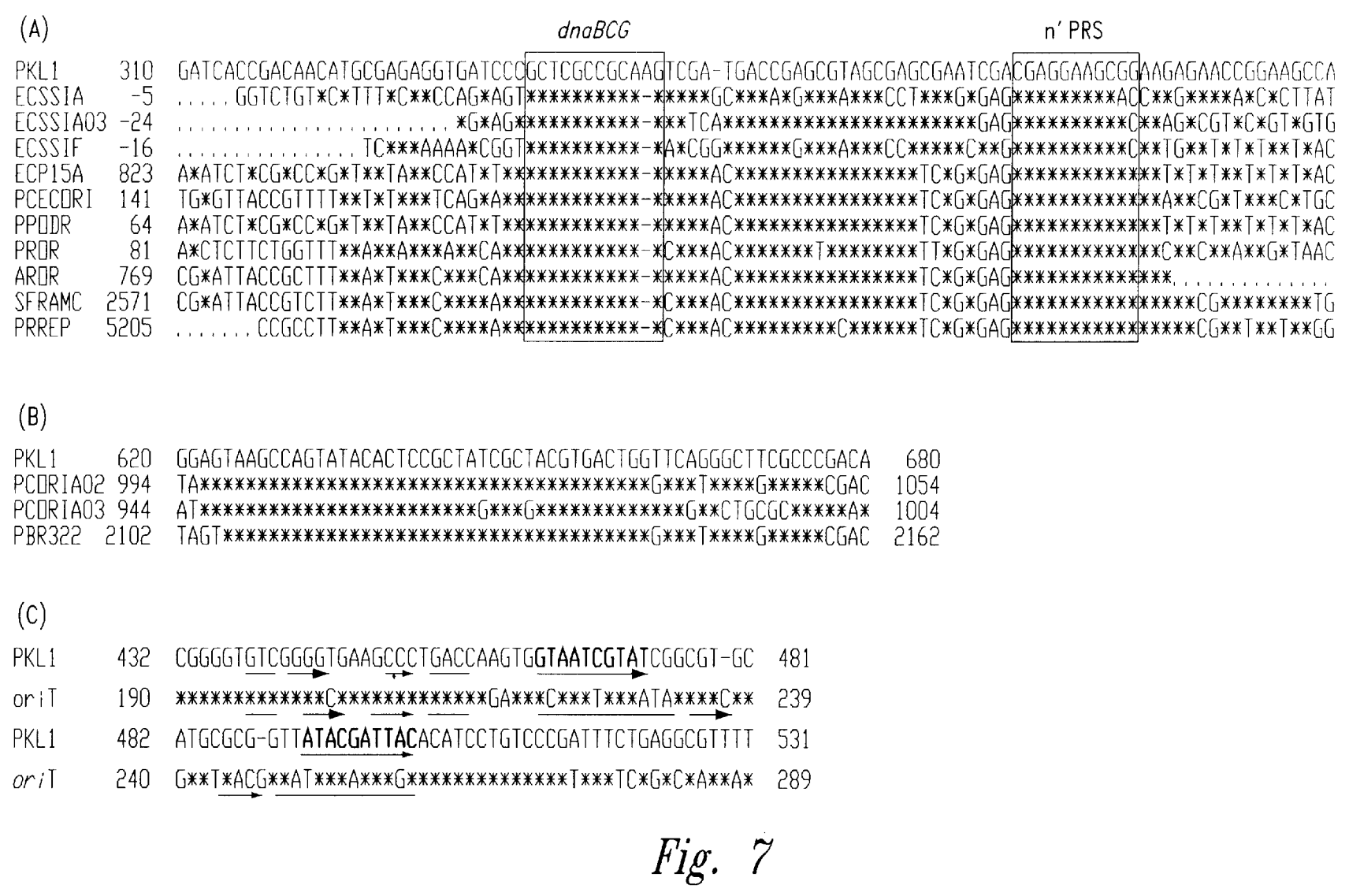
Figure 15A:
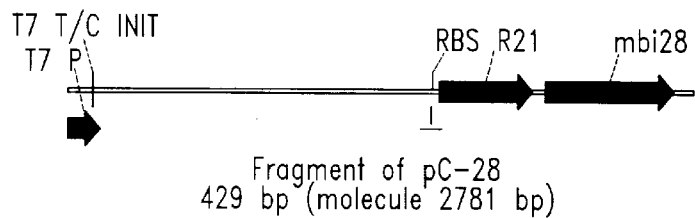
Figure 15B:
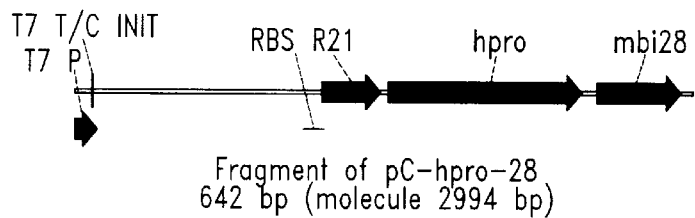
Figure 15C:
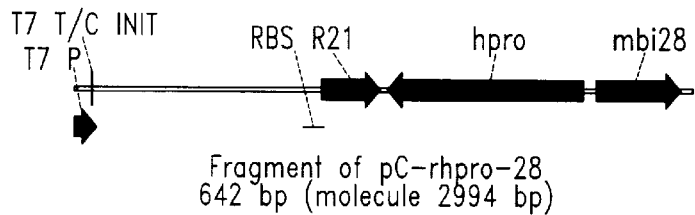
Figure 15D:
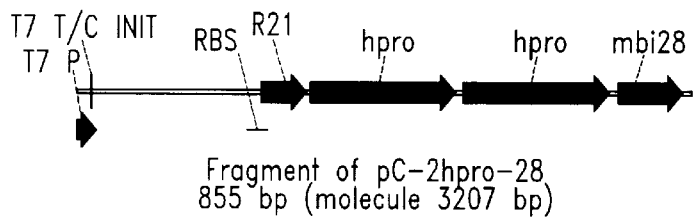
Figure 15E:
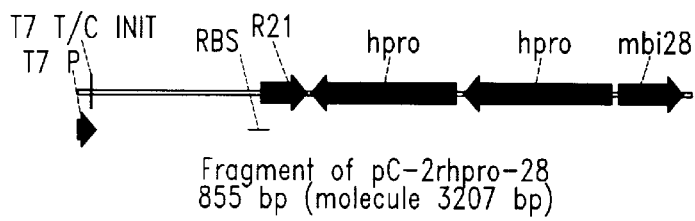

DNA sequence analysis of the region upstream of the repA gene reveals two putative ribosome binding sites (RBS) (Stormo et al., *Nucl. Acids Res.* 10:2971–2996 (1982)) at position 913 and 953 bp. The RBS in position 953 is in the repA gene and continues with an ATG start codon of an $ORF_{953-1051}$ that could theoretically encode a protein of $M_r$ 3998. The RBS in position 913 is clearly part of the repA gene. The complementary DNA strand contains no motifs similar to the *E. coli* RBS. A putative promoter is also located upstream of the repA gene (FIGS. 7, 15A and 15B). In addition, plasmid pKL1 contains a 10 bp perfect inverted repeat (stem-loop structure; $\Delta G_{25} = -10.2$ kcal mol$^{-1}$) in the same position as the R64 oriT 17 bp inverted repeat that plays a role in regulation of oriT, a gene is necessary for conjugative transfer of R64. In this regard, pKL1 is poorly mobilized by conjugative incT plasmid pKL7 present in the natural host of pKL1, *E. coli* KL4. Thus, this region of pKL1 is likely involved in plasmid mobilization.

Figure 5:
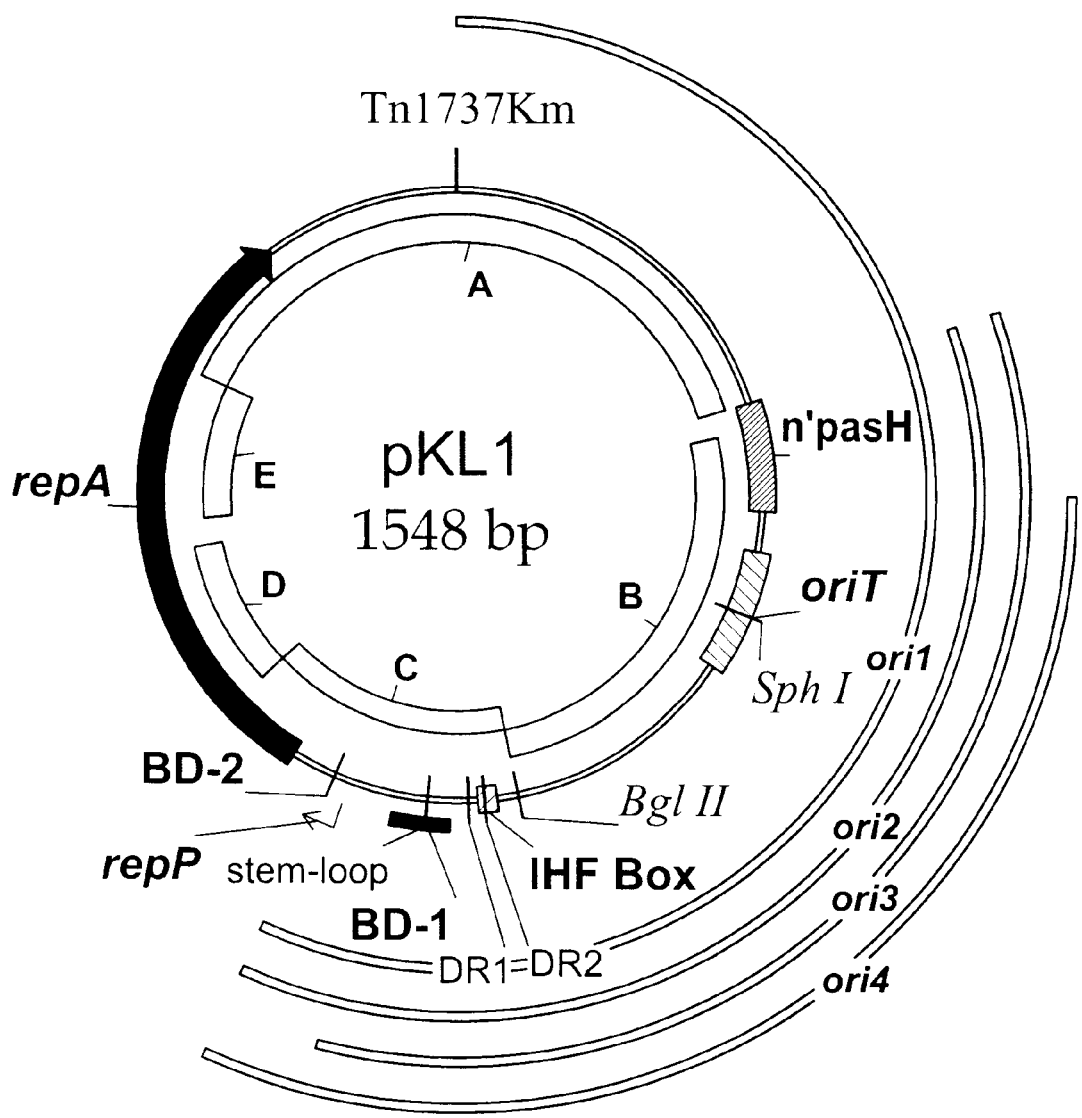
FIG. 5. Genetic map of pKL1. The circular permuted pKL1 genome, showing restriction sites BglII and SphII and DNA regions of interest. A, B, C, D and E represent the Sau3AI fragments A–E; repA—gene encoding RepA protein; repP promoter of the gene repA; BD-1, BD-2 are RepA binding sites; DR1, DR2 are direct repeats TGTTTTTT; stem-loop is a putative stem-loop structure; IHF box—IHF binding site; oriT—putative conjugation origin of replication; n'-pasH—single strand initiation site; ori1-4 represents fragments of pKL1 cloned to ColE1 type of plasmid, which were then tested for replication ability when RepA was provided from a heterologous plasmid in trans in polA1 mutant E. coli host in which only ori1 and ori2 were fully functional.

DNA and protein homology searches reveal no significant similarities to repA or RepA. However, there are short, but significant, similarities between pKL1 (315–410 bp) and the single strand initiation signals, ssiA, ssiF of plasmid F, ssiA of plasmids ColE2, p15A, ColE1, pACYC184 and pas-BL of pBR322 (FIG. 7A). (Marians et al., *J. Biol. Chem.* 257:5656–5662 (1982); Nomura et al., *Proc. Natl. Acad. Sci. USA* 79:3153–3157 (1982); Murotsu et al., Mol. Gen. Genet. 196:373–378 (1984); Bahk et al., *Plasmid* 20:266–270 (1988); Nomura et al., *Gene* 108:15–22(1991)). This same region of the pKL1 sequence is also similar to parts of the replication origins of plasmids RSF1030 (Som and Tomizawa, *Mol. Gen. Genet.* 187:375–383 (1982)) and R485 (Stalker and Helinski, *Plasmid* 14:245–254 (1985)), part of *Salmonella flexneri* 2 MDa plasmid (EMBL ACC M25995), and a region of the plasmid R100 repA gene (Otsubo et al., *Adv Biophys* 21:115–133 (1986)). In addition, there is a short region of homology between pKL1 (620–680 bp) and parts of the replication origins of plasmids ColA, ColD (Zverev et al., *Plasmid* 12:203–205 (1984)) and pBR322 (FIG. 7B) as well as a similarity of pKL1 (432–531 bp) and the oriT region of plasmid R64 (FIGS. 5 and 7C). Furthermore, a putative IHF binding site (IHF box) TAAGTGGTTGTTT (SEQ ID NO:25) is found at position 744–756 bp on the H strand (FIGS. 5, 13). The total of all these similarities represents only about 11% of the pKL1 DNA sequence.

Example 5

Expression, Purification and Microsequence Analysis Of RepA Protein

The protein RepA can be produced in abundance very easily and is very stable. Briefly, the repA gene is expressed in the T7 promoter system (Tabor and Richardson, *Biochemistry* 82:1074–1078 (1985)) using plasmids pBGL-R, pBGL73, pREP1, and pGP1-2 as the donor of T7 RNA polymerase (Table 1). The high efficiency of the repA RBS is apparent from the large amounts of RepA protein that are produced in this system. Whole cell lysates are analyzed for RepA by sodium dodecyl sulfate polyacrylamide gel electrophoresis (SDS-PAGE) and gel densitometry. The relevant gel band is a 17.9 kDa protein and represents more than 35% of total cell protein (FIG. 10). RepA is soluble in the cytoplasm, but when purified has a tendency to aggregate at low ionic strength.

*E. coli* XL1 Blue containing pBGL-R and pGP1-2 is cultivated at 28° C. overnight in T-broth with vigorous shaking. An equal volume of fresh prewarmed (42° C.) medium is added and incubation continued at 42° C. for two hours. Cells are harvested by centrifugation, washed with 50 mM Tris-HCl, 200 mM KCl, 1 mM EDTA, pH7.6, resuspended in 250 ml of the same buffer, and broken open in a French Press homogenizer at 1000 psi. The RepA-containing fraction is precipitated from the cleared cell lysate with 7.3% polyethylene glycol 8000 (Sigma) and collected by centrifugation at 15,000×g. The protein precipitate is resuspended in 100 ml of 50 mM Tris-HCl, 100 mM KCl, 1 mM EDTA, pH7.6 and loaded on a 200 ml DEAE cellulose column (Whatman). After rigorous washing with the loading buffer, RepA is eluted as a major peak from the column using a linear 0.2–1 M gradient of KCl. RepA is stored frozen at −80° C. at a concentration about 10 mg/ml in 50 mM Tris-HCl, 1 mM EDTA, 500 mM KCl, 5% glycerol.

Purified RepA is resolved by SDS-PAGE (FIG. 10, lane 3) and electrophoretically transferred to Immobilon PVDF membrane (Millipore) for direct N-terminal amino acid sequence analysis as previously described (Collinson et al., *J. Bacteriol.* 173:4773–4781 (1991)). Protein sequence analysis yielded the following 48 amino acid, N-terminal sequence:

MFIDSEKRLKQLSDEAKKNTEDLEE-
AKKNSRFTQVSKPGWERVREL LK. (SEQ ID NO:26)

RepA is unusually small ($M_r$ 17,960) compared to other known plasmid Rep proteins, which are normally in the 30–60 kDa range. RepA from pKL1 is predicted to have distinct hydrophobic and hydrophilic regions, which could lead to the formation of protein dimers or oligomers. Dimers of Rep proteins have been described for plasmid P1, F, R6K, pSC101, among others. In particular, the pSC101 RepA protein exists in both monomeric and dimeric forms. Monomers bind to direct repeat iterons near the replication origin, whereas dimers bind to sequences that autoregulate RepA synthesis. The equilibrium between monomer and dimer forms of RepA has a key role in determining its effect on the replication of pSC10.

Example 6

Effect of RepA on Incompatibility

Plasmids containing the Sau3AI fragment C (FIG. 5, FIG. 6) encompassing the putative inc region (plasmids pC, pC72 and pC73) or inc plus repA region (plasmid pBGL-F) of pKL1 are strongly incompatible with pKL1 and virtually completely eliminate pKL1. However, the copy number of pKL1 is significantly increased in the presence of the plasmid pBGL-R, which contains the inc and repA region. In pBGL-R, the repA gene is positioned immediately downstream of the lacP and T7 promoters, resulting in the constitutive production of the RepA protein in *E. coli* DH1 (FIG. 8, lanes 6 and 7). Thus, uncontrolled repA expression appears to override the incompatibility effect. This finding is verified by the plasmid pBGL73, in which repA is under control of the T7 promoter only and thus, for expression, requires the presence of T7 RNA polymerase encoded by plasmid pGP1-2. As expected, pBGL73 alone is strongly incompatible with pKL1, but in the presence of pGP1-2 the RepA protein is produced. These results indicate that the incompatibility of pKL1 is due to the titration of RepA by high copy number plasmids pBGL-F, pC, pC73 or pC72 and that RepA is involved in the regulation of plasmid replication as an initiator of pKL1 replication.

Example 7

Requirement for Integration Host Factor (IHF)

Higher-order nucleoprotein complexes are associated with many biological processes. In bacteria, the formation of these macromolecular structures for DNA recombination, replication, and transcription often requires not only the participation of specific enzymes and co-factors, but also a class of DNA-binding proteins collectively known as "nucleoid-associated" or "histone-like" proteins.

Examples of this class of proteins are IHF, H-NS, and Fis. pKL1Cm is used to assess whether the nucleoid associated proteins are required for pKL1 replication. Neither hns nor fis *E. coli* mutants has any effect on pKL1Cm replication. However, in vivo experiments with both IHF mutants (himA and himD) demonstrated that IHF is absolutely required for pKL1Cm replication. Analysis of the DNA sequence reveals a putative IHF binding site on the Sau3AI fragment C of pKL1 (FIG. 5). Gel retardation assays of the EcoRI-HindIII fragment of pC (corresponding to Sau3AI fragment C of pKL1, FIG. 6) confirm that this fragment contains an IHF binding site. The retardation of the relevant fragment is similar to the retardation of a 180 bp HindIII fragment from pGP1261 containing the phage Mu IHF binding site (FIG. 9).

Example 8

Location and DNA Sequence of the RepA Binding Sites

The binding site of the RepA protein on pKL1 is initially analyzed by Southwestern analysis. Two probes are prepared. The first probe is the BglII-BamHI fragment (857 bp) of pTZKL1 containing the repA gene (474 bp) plus 383 bp of pKL1. This fragment is self-ligated to create plasmid pDBGL. The second probe contains the remainder of pKL1 sequence. It is prepared as an EcoRI-XbaI fragment. As shown in FIG. 4, RepA binds to whole pKL1 DNA and exclusively to the BglII- BamHI fragment of pTZKL1 (FIG. 4, panels B, C and D). Further Southwestern analysis demonstrates that RepA binds to the Sau3AI fragment C of pKL1. No binding is detected to Sau3AI fragments A, B or D, and only weak binding is observed to the BamHI-EcoRI fragment of plasmid pREP1.

The shared motif of all these strong RepA binding fragments is a predicted stem-loop structure, inc ($\Delta G_{25}$=−33.8 kcal mol$^{-1}$), located upstream of a putative promoter of repA on the Sau3AI C fragment of pKL 1 (FIG. 5). The stem (16 bp) contains an 11 bp symmetric sequence, CATCCAG-GATG (SEQ ID NO:27), and the central part of the loop (14 bp) contains a 10 bp palindromic sequence, ACAACGTTGT (SEQ ID NO:28). This structure is a strong candidate as a binding site of the RepA protein. To verify binding, the in vivo effects on pKL1 replication of pREP1 versus pBGL-R and pBGL73 versus pREP73 are compared. Plasmids pBGL-R and pBGL73 carry repA and its upstream sequence with the stem-loop structure and repA under the control of native and lac or native and T7 promoters respectively. pREP1 and pREP73 contain a fragment of repA without its putative promoter(s) and the inc region but only repA is under control of the lac or T7 promoters respectively. pREP1 has the same effect on pKL1 as did pBGL-R and also induced the amplification of pKL1 copy number. pBGL73 is strongly incompatible with pKL1, however, pREP73 is compatible with pKL1 having no effect on its replication. In the presence of pGP1-2, both plasmids induce the amplification of pKL1. These results show that RepA binds exclusively to the region of pKL1 carrying a predicted stem-loop structure and potential promoter of repA gene.

Figure 6:
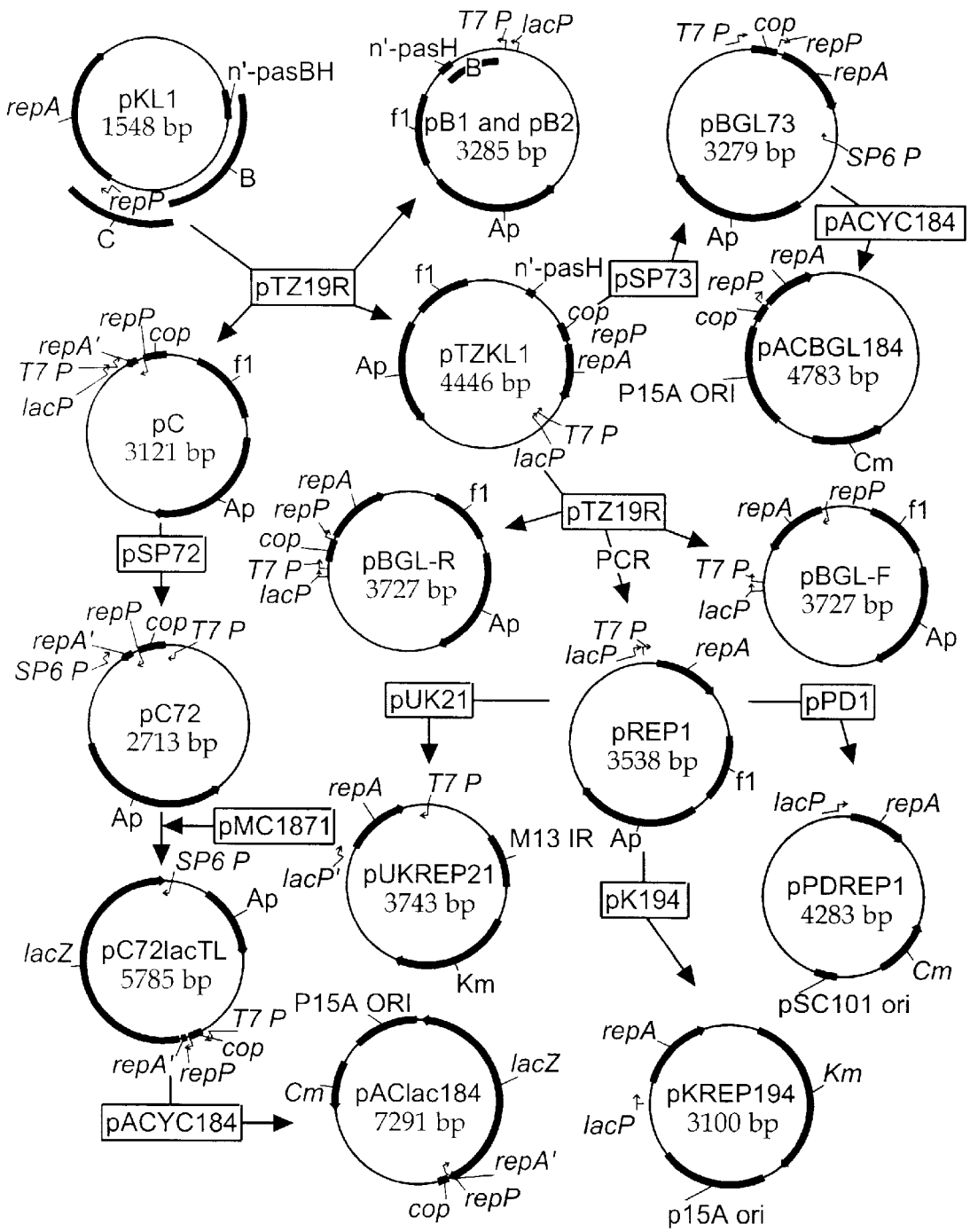
FIG. 6. Recombinant plasmids containing different fragments of pKL1 and replication helper plasmid.

Clearly, the regulation of pKL1 replication was mediated through some form of RepA—cop region DNA interaction, which could be analyzed by DnaseI footprinting and gel retardation assays. This was accomplished using the Sau3AI fragment C (FIG. 5) of pKL1 prepared by BamHI and EcoRI restriction digestion of pC (FIG. 6). This permitted [$\alpha$-$^{32}$P]-dATP labeling of only the EcoRI end using the Klenow fragment of DNA polymerase. DnaseI footprinting experiments were repeated several times with virtually identical results. In some cases a DNA sequencing reaction with pC as a template was used in parallel to map positions of DnaseI hot spots and regions protected by RepA. The sequencing primer, TCGAGCTCGGTACCCGG (SEQ ID NO:29), initiated reading of the sequence exactly at the first nucleotide of the Sau3AI fragment C of pKLI. A piperidine DNA cleavage reaction was also used to randomly hydrolyze labeled fragment C and to create a control reaction containing labeled fragments of all possible sizes. Some reactions were analyzed using a 75 cm polyacrylamide gels where it was possible to identify each nucleotide of fragment C. FIG. 12 shows a typical result from a standard 40 cm gel. The binding of RepA to the Sau3AI fragment C of pKLl induced an extensive and obvious DNA bend, which exposed three 2–3 bp hot spots to DNAse I. Symmetry of the DnaseI footprint image suggested that the computer predicted, putative stem-loop structure was indeed formed. A stem (16 bp) of the putative stem-loop structure ($\Delta G_{25}1=-33.8$ kcal mol$^{-1}$) contains the symmetric sequence CATCCAGGATG, (SEQ ID NO:27) and the central part of the loop (14 bp) contains a 10 bp palindromic sequence ACAACGTTGT (SEQ ID NO:28). The part of sequence, CAACGTT, designated binding domain I (BD-1), of the loop was clearly protected against DNAse I activity and therefore is a strong candidate as a binding site of RepA. In addition, the same sequence, CAACGTT, (binding domain II, BD-2) was found in the repA promoter region. The Dnase I digestion pattern indicated that this region was also protected by RepA. The protection pattern of this domain and the subsequent region suggested an iterative type of RepA binding. There were four distinct regions of protection separated by about 2 bp accessible to DNAse I. The DNAse I digestion pattern following this region showed no differences for DNA digested in the presence or absence of RepA (FIG. 12).

The existence of distinct RepA binding sites was examined further using gel retardation assays. The labeled Sau3AI fragment C of pKL1 was incubated with different concentrations of RepA and the gel retardation of the resulting RepA-DNA complexes were detected using PAGE and radiography. The results showed patterns characteristic of multiple protein binding (FIG. 12).

To assess the stoichiometry of RepA-DNA complexes of fragment C the methods of {Orchard, 1993 #658} were used, in a series of gel retardation assays at various polyacrylamide concentrations to indicate the number of protein units bound in the protein-DNA complex. RepA and IHF were independently bound to Sau3AI fragment C and the resulting DNA-protein complexes analyzed by electrophoresis. The electrophoretograms were essentially the same as shown in FIG. 12. The result for IHF-DNA complex was as expected: the mass approximated the predicted MW of IHF heterodimer. However, the calculated molecular masses for RepA-DNA complexes did not correspond specifically to a monomer, dimer or any simple oligomer of RepA bound to fragment C. Thus it was assumed that RepA-DNA complexes have an anomalous electrophoretic mobility possibly due to the extreme bending of DNA caused by the RepA binding. Therefore a different approach was taken.

In vitro studies with purified RepA have shown that it has a strong tendency to oligomerize. It was further assumed that RepA might form dimers and/or oligomers also in vivo. Therefore a novel test, which we call the "Pacific-Southwestern" blot assay (cross-linked protein Southwestern assay), was developed in order to study the interaction of RepA monomers and crosslinked oligomers with target pKL1 DNA probes. A probe containing only BD-1 bound preferentially to monomers and crosslinked dimers and to lesser extent to lower oligomers of RepA. A probe containing only BD-2 bound preferentially to higher oligomers of the crosslinked RepA. A probe with a complete cop region, containing both BD-1 and BD-2, bound evenly to all RepA forms (FIG. 12).

IHF and RepA Cooperativity

IHF is essential for pKL1 replication and an active IHF box was also found in the cop region. It was thought that IHF and RepA might somehow cooperate in the regulation of plasmid replication. Thus gel retardation assays using both IHF and RepA were performed. The labeled fragment C of pKL1 was incubated with different concentrations of IHF and RepA and the resulting protein-DNA complexes analyzed by electrophoresis and radiography (FIG. 12). No evidence for a DNA-protein complex was found which could be ascribed to both IHF and RepA binding. However, singular IHF or RepA complexes were readily detected and the minimal concentration of RepA necessary for binding to fragment C was reduced to 50% in the presence of low concentrations of IHF. It was also observed that IHF was almost completely released from a DNA complex after the addition of a relatively small amount of RepA; thus IHF might be considered a catalyst of the RepA-DNA interaction.

Example 9

A Functional ssi Signal

Plasmids pB1 and pB2 are used for recloning the Sau3AI fragment B of pKL1 containing the putative single strand initiation signal into M13Δlac110 phage in both orientations. The plaque morphology and titer of resulting phages M13ΔlacB1 and M13ΔlacB2 are determined. Normally, defective M13Δlac110 phage forms small plaques. However, when a functional ssi region is cloned into this phage, both plaque size and phage titers are increased. The results are presented in the Table 2.

TABLE 2

| Phage | Titer (pfu/ml) | ssi Factor | Plaque morphology |
|---|---|---|---|
| M13Δlac110 | $1.0 \times 10^8$ | 1 | Small |
| M13ΔlacB1 | $0.8 \times 10^{10}$ | $10^2$ | Large |
| M13ΔlacB2 | $1.2 \times 10^{10}$ | $10^2$ | Large |

The results reveal that functional ssi signals in pKL1 act in both orientations. Particularly apparent is the ssi signal, n'-pasH homologous to the φX174 type primosome assembly site (pas) with the dnaB, dnaC and dnaG protein-dependent initiation and n' protein (PriA) recognition sequences (FIG. 7A). This sequence of pKL1 is likely able to form a secondary structure very similar to the consensus structure for group II n'-pas represented by ColE1 ssiA. Primosome assembly sites are important for efficient, lagging-strand synthesis during plasmid DNA replication, as they are the sites for formation of multiprotein, bi-directional DNA replication priming/helicase (3'-5' and 5'- 3' activities) complexes. Therefore, the n'-pasH equivalent of pKL1 likely initiates RNA primer synthesis in both orientations. However, a second ssi may be present and account for the bidirectionality. Sequence motifs characteristic of plasmid G sites, which are directly recognized by the *E. coli* primase (DnaG) and which conduct the synthesis of an RNA primer required for leading DNA strand synthesis, are not present. On the contrary, an unusual high homology of pKL1 (620–680 bp) with ColA, ColD and pBR322 plasmids (FIG. 7C) is found and this region could be a candidate for an as yet unknown ssi activity.

Example 10

Amplification of the Copy Number of pKL1 Using a Helper Plasmid

Strain *E. coli* DH1 that contains plasmid pKL1 is transformed with pTZ19R, pGP1-2 or pBGL-R and with the combination of plasmids pTZIR+pGP1-2 or pBGL-R+pGP1-2. Plasmids pGP1-2 and pTZ19R have no effect on the pKL1 copy number (FIG. 8, lanes 3 and 5). However plasmid pBGL-R employing the repA gene under lacP control significantly increased the copy number of pKL1

(lane 7). Plasmid pBGL-R also contains the T7 promoter, and in the presence of pGP1-2, the expression level of RepA and the copy number of pKL1 is increased even higher (lane 6). If pBGL-R retains the copy number of its parent plasmid pTZ19R, approximately 500 copies, pKL1 is amplified to >1500 copies.

This phenomenon was further quantified using several helper plasmids with different ability to express RepA from lacP. Strain *E. coli* DH 11 is transformed with pKREP194 (low copy number helper plasmid with relatively low expression level of RepA), pUKREP21 (high copy number helper plasmid with moderate level of expression of RepA) and pREP1 (high copy number helper plasmid with the highest level of expression of RepA). The expression levels of RepA are further modulated by IPTG and/or the presence of F'lacP$^q$ plasmid, which produces higher levels of the lac repressor. Strains are cultivated in the presence or absence of different concentrations of IPTG, and plasmid DNAs are isolated, resolved by agarose gel electrophoresis and quantified by densitometry. The relative increase of the copy number of pKL1 are calculated and the results shown in FIG. 11. pKL1 can increase its copy number more than 90-fold and likely as high as 3000 copies of pKL1 per cell are present.

Rep proteins of several plasmids, such as R1, pSC101, R6K, R1ts, F, RSF1010, and the pLS1 plasmid family play crucial roles in the initiation of plasmid replication. The phenomenon of rampant proliferation ("RAMP") of pKL1 due to the increased levels of initiator protein, RepA, is similar to the "runaway" replication of plasmid R1 (Gustafsson and Nordstrom, *J. Bacteriol.* 141:106–110 (1980); Givskov and Molin, *Mol. Gen. Genet.* 194:286–293 (1984)). However, the highly exaggerated replication of pKL1 is not lethal to the host cell in contrast to runaway mutants of the R1 plasmid (Uhlin et al., *Gene* 6:91–106 (1979)). Furthermore, Rep proteins of some plasmids exhibit bifunctional activities, binding to the ori region, which leads to the initiation of replication, and binding to the promoter region of rep, autoregulating expression. RepA of pKL1 may also be bifunctional, because no regulatory ctRNA (Novick, *Microbiol Rev* 4:381–395 (1987)) or protein repressor are known. Although pKL1 does not contain iteron-like repeats for RepA binding, there is a 7 bp sequence CAACGTT, which is repeated in the loop of the predicted stem-loop structure (Binding domain BD-1) and then in +1 region of promoter repP (FIGS. 5 & 12A). RepA binds to BD-1 at the stem-loop structure to initiate replication and subsequently binds to the BD-2 to autoregulate the repA gene. DNA binding of RepA likely depends on a strictly defined secondary DNA structure.

Example 11

Transcriptional Fusion of lacZ to the repA Promoter Region

Computer analysis reveals a putative promoter located upstream of repA on the Sau3AI fragment C (FIG. 5). To confirm the existence of promoter activity, the plasmid pClacTC carrying a promoter-less lacZ gene, but still containing an RBS, is constructed in pSP72 behind the T7 promoter. The lacZ gene is located downstream after the codon 21 of repA on the Sau3AI fragment C. Thus, there is no promoter activity upstream of the C fragment in the absence of T7 RNA polymerase. The resulting phenotypically Lac+*E. coli* XL1 recombinant clones contain pClacTC. The range of β-galactosidase enzyme activity in cell lysates is 7.8–9.2 kU/ml. This result documents an existence of the promoter within Sau3AI fragment C upstream of repA.

Example 12

Autoregulation of repA Gene In Vivo

The relative copy number of pKL1 was compared to the low copy plasmid pACYC184 and high copy pSP73. Plasmid DNA was isolated from *E. coli* DH11 harboring pKL1 and pACYC184 or pSP73 and was analyzed by agarose electrophoresis and densitometry from which the relative copy number of pKL1 was calculated. pKL1 had a copy number higher than pACYC184 but much lower than pSP73. Plasmid pORI1 containing a repA-less replicon of pKL1 from pSPori1 and Km$^r$ was prepared. This plasmid was found to replicate only in the presence of RepA provided in trans and its replication was stable in the presence of pREP1 or pPDrep1. The copy number of pORI1 was high in the presence of pREP1 (high expression of repA) and relatively low in the presence of pPDrep1 (low expression of repA). This demonstrated that pORI1 replication could be supported by a relatively low concentration of RepA. This invoked the idea of determining whether the complete repA including the upstream cop region and the repA promoter cloned to pACYC 184 or pSP73 could support pORI1 replication. These relevant constructs simulated the two extreme situations of the copy number below and above normal for the repA regulatory circuit and consequently for pKL1 replication. *E. coli* XL1 Blue was cotransformed with a combination of the resulting recombinant plasmids pACBGL184 or pBGL73 with pORI1 and selected on media containing Ap and Km. Transformants were obtained only for the combination pACBGLI84/pORI1. The high copy plasmid, pBGL73, did not support replication of pORI1. The results indicate that repA was sufficiently expressed to support pORI1 replication only when present at a gene dose lower than the natural copy number of pKL1 and the system cop/repA in a high copy number plasmid was repressed.

Example 13

Construction of repA Based Expression System for Antibacterial Cationic Peptide MBI28

Plasmid pC72 (FIG. 14), based on cloning vector pSP72 (Promega), containing the part of repA of pKL1 was used to construct a series of plasmids containing the sequence encoding cationic peptide MBI28 (Table 1). Briefly, the MBI28 gene from plasmid pA-CEMA was directly fused to repA fragment R21 resulting in plasmid pC-28. This plasmid potentially encodes a small protein R21-28 (Table 1), but when the T7 promoter system was used to induce expression of this protein, no expression was detected. Plasmid pC-28 was stable in *E. coli* XL1Blue, however in the presence of plasmid pGP1-2, especially at 42° C., it was eliminated. pGP1-2 encodes T7 RNA polymerase and under the control of lambda promoter and thermosensitive repressor CI857 it can greatly induce T7 promoter based expression at 42° C.

In order to stabilize the expression plasmid and fusion protein, a DNA sequence encoding the protecting region Hpro (Table 1) based on the published Prepro region from the gene of human defensin (Piers, K. L., Brown, M. H. and Hancock, R. E. W., *Gene* 134:7–13, 1993) was synthesized and inserted between MBI28 and R21 sequence into a BamHI cloning site resulting in plasmid pC-hpro-28 (FIG. 15). Hpro sequence in addition to the original Prepro included six histidine designed as a tag for metal chelate chromatography for purification of the fusion protein. The fusion protein R21-hpro-28 (Table 1) was also not detected when the T7 promoter system was induced, but plasmid pC-hpro-28 remained stable. In the process of cloning of the hpro fragment several plasmids with different number and orientation of hpro were selected and used to test for expression of fusion proteins (FIG. 16). Plasmid pC-2hpro-28 encodes fusion protein based on fusion of R21, two Hpro in tandem and MBI128, which was expressed at a good level (Table 1, FIG. 16). Plasmid pC-2rhpro-28 contains the R21 fragment, two hpro sequences inserted in the inverted orientation and the sequence encoding MBI28 (Table 1, FIG. 16). This mean that inverted hpro encodes different amino acid sequence (Table 1). Expression of that protein was not detected. Plasmid pC-rhpro-28 encoding protein R21-rhpro-28 (Table 1, FIG. 16) with inverted hpro was also selected and the expression test was negative.

Simultaneously experiments were carried out with larger RepA fragment designated R78. This fragment was generated by PCR and the natural promoter of repA gene and the putative upstream stem-loop were deleted. Plasmid pR78-hpro-28 was then tested for expression of the fusion protein R78-hpro-28 (Table 1) and results were positive. In this case, one Hpro region was enough to stabilize the fusion protein.

The expression system was further studied and the necessity of RepA fragment R21 to achieve expression of fusion proteins containing two Hpro domains was questioned. Therefore, the fragment encoding tandem Hpro fused to MB128 gene was generated by PCR and cloned to plasmid pT7-7. Plasmid pT7-7, a T7 promoter system, contains all necessary transcription and translation signals for expression. The relevant fragment was fused directly downstream of the start codon. No expression of 2Hpro-28 fusion protein was detected when the T7 promoter system of pT7-7 was induced.

Described series of experiments demonstrated that Hpro alone has no potential to protect fusion proteins containing MBI28, which are smaller than 76 amino acids. It was also shown that the tandem Hpro domain has no potential for expression of cationic peptide MB128. Properties of a carrier protein, which must consist of at least 75 aa are important for stability of expression system, even if the carrier protein itself cannot protect MBI28 fusion. Leader sequences R21 and R78 based on RepA were clearly proven to be important for good expression and stability.

Construction of the Universal Expression System

Since the previously described system for expression of MBI28 was constructed as a cassette system, there were unwanted BamHI restriction sites preventing use of this plasmid for cloning another peptide genes. Furthermore, the R21 upstream region also contained the repA promoter and a putative stem-loop region, which could interfere with efficient transcription. Therefore the expression plasmid containing R21 and two hpro regions was changed in such a way that only necessary restriction sites were present, the upstream region of R21 was deleted and a new plasmid was used as the universal cloning and expression vector for cationic peptides. Following that, peptides MBI128, MBI31 and MBI11 were expressed.

At first plasmids pC-hpro-28 and pC-2hpro-28 were modified. PCR was use to amplify DNA fragment containing R21-hpro-28 region, but the upstream region of R21 was deleted. PCR primers were TGGCTTAGAATTCAAC-CAACGTTAG (SEQ ID NO:30) and AGAACTCGAG-CAGCTGAAGCTTAG (SEQ ID NO:31). PCR of thirty cycles (94° C. 0 sec.; 50° C. 0 sec. and 72° C. 15 sec.) was performed in Idaho Technology capillary thermo-cycler in 10 ml reaction volume using Idaho standard protocol. PCR products were digested with BamHI and EcoRI and cloned into pSP72 resulting in plasmids pR21-hpro-28 and pR21-2hpro-28. The second plasmid was used for expression of fusion protein R21-2hpro-28 and expression level was compared with previous construct pC-2hpro-28. Expression was clearly improved (FIG. 16, lane 3 versus lane 4). The next step was to eliminate the unwanted BamHII restriction sites. The hpro fragment was modified by PCR using pC-hpro-28 as a template and primers CGTTGCAGAT-CTACATCACCATCACCATCA (SEQ ID NO:32) and TGCGGATCCCCGTTTTTCCTTGAGCCTGGATGCTT-TGGA-GCCAACGTTTC, (SEQ ID NO:33) reaction was performed in an MJ-Research PTC-100 Thermo-cycler in 50 ml reaction volume and 30 cycles of 94° C. 30 sec.; 50° C. 30 sec. and 72° C. 30 sec. PCR product was digested with BglII and BamHI and cloned into pR21hpro-28 digested with BamHI. This replaced the original hpro fragment with BamHI ends with a new fragment and thus one BamHI site was eliminated by the BglII-BamHI ligation. This cloning procedure was repeated and the resulting plasmid was named pR2h-28. Finally EcoRI-BamHI fragment containing R21 and two hpro regions was recloned to pSP72 resulting in the universal expression vector pR2h-B1.

TABLE 1

AMINOACID SEQUENCES OF FUSION PROTIENS AND RELEVANT PEPTIDES.

| Peptide/Fusion protien molecular weight (MW) | aa sequence | | expression |
|---|---|---|---|
| MBI28 MW 3051 | KWKLFKKIGIGAVLKVLTTGLPALKLTN | (SEQ ID NO:34) | N\A |
| MBI31 MW 2081 | GKPRPYSPIPTSPRPIRY | (SEQ ID NO:35) | N\A |
| MBI11 MW 1879 | ILKKWPWWPWRRK | (SEQ ID NO:36) | N\A |
| R21—28 MW 6024 | MFIDSEKRLKQLSDEAKKNTEDPHMKWKLFK KIGIGAVLKVLTTGLPALKLTN | (SEQ ID NO:37) | No |
| Hpro MW 7751 | HHHHHHRTLAILAAILLVALQAQAEPLQARA DEVAAAPEQIAADIPEVVVSLAWDETLAPKHP GSRKNGDPH | (SEQ ID NO:38) | N\A |

TABLE 1-continued

AMINOACID SEQUENCES OF FUSION PROTIENS AND RELEVANT PEPTIDES.

| Peptide/Fusion protien molecular weight (MW) | aa sequence | | expression |
|---|---|---|---|
| R21-Hpro-28 MW 13621 | MFIDSEKRLKQLSDEAKKNTEDPHHHHHHRT<br>LAILAAILLVALQAQAEPLQARADEVAAAPEQ<br>IAADIPEVVVSLAWDETLAPKHPGSRKNGDPH<br>MKWKLFKKIGIGAVLKVLTTGLPALKLTN | (SEQ ID NO:39) | No |
| R21-2Hpro-28 MW 21217 | MFIDSEKRLKQLSDEAKKNTEDPHHHHHHRT<br>LAILAAILLVALQAQAEPLQARADEVAAAPEQ<br>IAADIPEVVVSLAWDETLAPKHPGSRKNGDPH<br>HHHHHRTLAILAAILLVALQAQAEPLQARADE<br>VAAAPEQIAADIPEVVVSLAWDETLAPKHPGS<br>RKNGDPHMKWKLFKKIGIGAVLKVLTTGLPA<br>LKLTN | (SEQ ID NO:40) | Yes |
| R21-2rhpo-28 MW 20993 | MFIDSEKRLKQLSDEAKKNTEDPRFSLSLDAL<br>EPTFRPMQGKQPLLGCQLQSAPGLLQPHQLLP<br>GVAQPGPAGPPGEWQQGWRGSCDGDGDVDP<br>RFSLSLDALEPTFRPMQGKQPLLGCQLQSAPG<br>LLQPHQLLPGVAQPGPAGPPGEWQQGWRGSC<br>DGDGDVDPHMKWKLFKKIGIGAVLKVLTTGL<br>PALKLTN | (SEQ ID NO:41) | No |
| R78-hpro-28 MW 19622 | MFIDSEKRLKQLSDEAKKNTEDLEEAKKNSRF<br>TQVSPKGWERVRELLKDSQGISALKLYSFLAD<br>HIDPTCGAVVADPHHHHHHRTLAILAAILLVA<br>LQAQAEPLQARADEVAAAPEQIAADIPEVVVS<br>LAWDETLAPKHPGSRKNGDPHMKWKLFKKI<br>GIGAVLKVLTTGLPALKLTN | (SEQ ID NO:42) | |
| R78-rhpro-28 MW 19509 | MFIDSEKRLKQLSDEAKKNTEDLEEAKKNSRF<br>TQVSPKGWERVRELLKDSQGISALKLYSFLAD<br>HIDPTCGAVVADPRFSLSLDALEPTFRPMQGK<br>QPLLGCQLQSAPGLLQPHQLLPGVAQPGPAGP<br>PGEWQQGWRGSCDGDGDVDPHMKWKLFKKI<br>GIGAVLKVLTTGLPALKLTN | (SEQ IN NO:43) | |

Example 14

Cloning and Expression of Cationic Peptides MBI31 AND MBI11

Plasmid pR2h-B1 was digested with BamHI and HindIII and synthetic DNA fragments with identical ends encoding MBI31 or MBI11 were ligated resulting in plasmids pR2h-31 and pR2h-11 respectively. E. coli XL1 Blue was then cotransformed with pGP1-2 and either pR2h-31 or pR2h-11, resulting in relevant production strains. Strains were temperature induced at 42° C. for 2 hours and whole cell lysate and partly purified inclusions of fusion proteins in SDS buffer were analysed by SDS-PAGE (FIG. 17). 1.5 ml of induced cell cultures were harvested in 1.5 ml eppendorf tubes by microfuging at 13,000 rpm for 2 min. Cell pellets were resuspended in 1.0 ml lysis buffer and sonicated three times for 1 min each at an amplitude setting of ~10. The sonicated fraction containing inclusion bodies was sedimented by microfuging at 8000 rpm (6000×g) for 5 min. at 4° C.; the pellet was resuspended in 1 ml of Triton X-100 solution and briefly sonicated, and the insoluble material was sedimented by microfuging. The pellet was washed with water and than extracted with organic extraction solution by sonication. Insoluble material was sedimented by microfuging and the supernatant was transferred to two clean 1.5 ml eppendorf tubes (i.e., ~500 ul in each tube) and evaporated to dryness in a Speed-Vac. The dry residue was resuspended in 100 ul of SDS-PAGE sample buffer and 10 ml was loaded on a 15–20% gel for analysis.

Example 15

Synthesis of the DNA Fragment Encoding Hpro

Two long antiparallel oligonucleotides 105 nt (SYN-U) and 102 nt (SYN-L) with a homology overlap of 22 nt were synthesized using an ABI PCR Mate DNA synthesizer and associated chemicals and protocols. Two PCR primers were also synthesized, one homologous to the 5' end of each long oligonucleotide, further lengthening the final product. A PCR reaction with 0.5 pmol of each long oligonucleotide and 5 pmol of each primer in a 10 ml reaction volume was set up using the standard reaction mix recommended by the Idaho Technologies PCR protocol. The annealing temperature of the long oligonucleotide overlap was 64° C. and the annealing temperature of the PCR primers was 72° C. Therefore PCR cycling was performed in two steps: one cycle 94° C., 0 sec.; 65° C., 0 sec. and 74° C., 15 sec. and then thirty cycles 94° C., 0 sec., 72° C., 0 sec. and 74° C., 15 sec. The idea of hpro synthesis is shown in following diagram. The PCR product was then cloned into vector pTZ 19R (Pharmacia) and the DNA sequence was verified by standard methods. Taq polymerase was purchased from Promega.

5' BamHI
5' BamHI
SYN-U: (SEQ ID NO:44)
ACCATCACAG GACCCTCGCC ATCCTTGCTG CCAT-TCTCCT GGTGGCCCTG CAGGCCCAGG CTGAGC-CACT CCAGGCAAGA GCTGATGAGG TTGCAG-CAGC CCCGG
SYN-L: (SEQ ID NO:45)
TGAGCCTGGA TGCTTTGGAG CCMCGTTTC GTC-CCATGCA AGGGAAACAA CCACTTCTGG GATGT-CAGCT GCMTCTGCT CCGGGGCTGC TGCMC-CTCA TC

PCR-U (SEQ ID NO:46):
CGAGGATCCA CATCACCATC ACCATCACAG GAC-CCTCGCC ATCCTTGCTG
PCR-L (SEQ ID NO:47):
TGCGGATCCC CGITTIICCT TGAGCCTGGA TGCIIIG-GAG CCAACGIIIC

Example 16

Synthesis of the DNA Fragments EncodinG MBI31 AND MBI11

Two oligonucleotides, MBI31 and MBI11, and two PCR primers, U and L, were synthesized;
MBI31:(SEQ ID NO:48)
TTTAACGGGGATCCGCATATGGGTAAACCGCGTC-CGTATAGCCCGATCCCGACCAG CCCGCGTC-CGATCC GTTATTAAGCTTGATATCTTGGTACCT-GCG
MBI11:(SEQ ID NO:49)
T T T A A C G G G G A T C C G T C T C A T A T G A T C C T G AAAAAATGGCCGTGGTGGCCGTGGCGTCG TAAAAATGCTT GATATCTTGGTACCTGCG
U: (SEQ ID NO:50)
TTTAACGGGGATCCGCATATG
L: (SEQ ID NO:50)
CGCAGGTACCAAGATATCAAGCTTA The PCR reaction contained about 20 ng of template (MBI31 or MBI11) and 2.5 pmol of each PCR primers in a 50 ml reaction volume. Taq polymerase, dNTPs and reaction buffer were purchased from Pharmacia. The PCR reaction was performed with 30 cycles 94° C., 30 sec., 57° C., 30 sec., 74° C., 30 sec. and 1 min. at 74° C. at the end of cycling. The PCR products were designed with BamHI and HindIII restriction sites for cloning into pR2h-B1 expression vector in frame with the carrier protein.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic acid molecule which encodes a repA protein, wherein said nucleic acid molecule is selected from the group consisting of:
   (a) a nucleic acid molecule which encodes a protein comprising the amino acid sequence of RepA wherein said protein is encoded by nucleotides 913 to 1386 of Sequence I.D. No: 19;
   (b) an isolated nucleic acid molecule that detectably hybridizes to the nucleic acid molecule of (a) or its complementary strand under conditions of 5×SSPE, 0.5% SDS, 1×Denhardt's, at 65° C. or equivalent salt and temperature conditions;
   (c) an isolated nucleic acid molecule that encodes a protein that has greater than 75% sequence homology to the protein encoded by the nucleic acid molecule according to (a); and
   (d) a nucleic acid molecule that, due to degeneracy of the genetic code, encodes a protein encoded by the nucleic acid molecule according to (b) or (c).

2. A vector that contains a nucleic acid molecule according to claim 1.

3. The vector according to claim 2, further comprising a heterologous nucleic acid molecule.

4. A host cell that contains a vector according to claim 2.

5. A vector that directs the expression of a nucleic acid molecule according to claim 1.

6. The vector according to claim 5, further comprising a heterologous nucleic acid molecule.

7. A host cell that contains a vector according to claim 5.

8. A vector which contains a promoter recognition sequence of the protein encoded by the isolated nucleic acid molecule according to claim 1.

9. A vector designated pKL1.

10. The vector according to any one of claims 9 or 8, further comprising a heterologous nucleic acid molecule.

11. A host cell that contains a vector according to any one of claim 9 or 8.

* * * * *